United States Patent
Cham et al.

(10) Patent No.: US 12,357,649 B2
(45) Date of Patent: Jul. 15, 2025

(54) GLYCOALKALOID COMBINATIONS AND VARIOUS USES THEREOF

(71) Applicants: Bill Elliot Cham, Efate (VU); Tania Robyn Chase, Efate (VU); Kai Elliot Cham, Sheldon (AU)

(72) Inventors: Bill Elliot Cham, Efate (VU); Tania Robyn Chase, Efate (VU); Kai Elliot Cham, Sheldon (AU)

( * ) Notice: Subject to any disclaimer, the term of this patent is extended or adjusted under 35 U.S.C. 154(b) by 1176 days.

(21) Appl. No.: 16/081,290

(22) PCT Filed: Mar. 3, 2017

(86) PCT No.: PCT/AU2017/050188
§ 371 (c)(1),
(2) Date: Aug. 30, 2018

(87) PCT Pub. No.: WO2017/147659
PCT Pub. Date: Sep. 8, 2017

(65) Prior Publication Data
US 2021/0260087 A1  Aug. 26, 2021

(30) Foreign Application Priority Data
Mar. 3, 2016  (AU) .................. 2016900798

(51) Int. Cl.
*A61K 31/706* (2006.01)
*A61K 9/00* (2006.01)
(Continued)

(52) U.S. Cl.
CPC .......... *A61K 31/706* (2013.01); *A61K 9/0014* (2013.01); *A61K 9/06* (2013.01);
(Continued)

(58) Field of Classification Search
CPC .... A61K 9/0014; A61K 31/706; A61K 47/36; A61K 31/19; A61K 31/60; A61K 31/17; A61K 47/06; A61K 47/10; A61K 9/107
See application file for complete search history.

(56) References Cited

U.S. PATENT DOCUMENTS

| 8,158,138 B1 | 4/2012 | Landau et al. |
| 2004/0053857 A1 | 3/2004 | Carter et al. |
| 2004/0220115 A1* | 11/2004 | Cham ............... A61K 31/58 |
| | | 514/26 |

FOREIGN PATENT DOCUMENTS

| EA | 10546 B1 | 10/2008 |
| RU | 2279880 C2 | 7/2006 |
(Continued)

OTHER PUBLICATIONS

Frank; "Xanthan Gum: A Multifaceted Polysaccharide"; 2015; https://knowledge.ulprospector.com/2099/fbn-xanthan-gum-a-multifaceted-polysaccharide/ (Year: 2015).*
(Continued)

*Primary Examiner* — Timothy P Thomas
(74) *Attorney, Agent, or Firm* — Schwegman Lundberg & Woessner, P.A.

(57) ABSTRACT

The present invention relates to the use of glycoalkaloids, such as solasonine and solamargine, in treatment of cancer such as skin cancer, and to compositions for use in such treatment. More particularly the present invention relates to providing an improved, substantially stable formulation for the glycoalkaloids which minimises or reduces degradation of these active molecules.

18 Claims, 1 Drawing Sheet

(51) Int. Cl.
| | |
|---|---|
| A61K 9/06 | (2006.01) |
| A61K 31/05 | (2006.01) |
| A61K 31/121 | (2006.01) |
| A61K 31/17 | (2006.01) |
| A61K 31/19 | (2006.01) |
| A61K 31/194 | (2006.01) |
| A61K 31/205 | (2006.01) |
| A61K 31/22 | (2006.01) |
| A61K 31/327 | (2006.01) |
| A61K 31/60 | (2006.01) |
| A61K 33/04 | (2006.01) |
| A61K 36/47 | (2006.01) |
| A61K 47/36 | (2006.01) |
| A61P 35/00 | (2006.01) |

(52) U.S. Cl.
CPC ............ *A61K 31/05* (2013.01); *A61K 31/121* (2013.01); *A61K 31/17* (2013.01); *A61K 31/19* (2013.01); *A61K 31/194* (2013.01); *A61K 31/205* (2013.01); *A61K 31/22* (2013.01); *A61K 31/327* (2013.01); *A61K 31/60* (2013.01); *A61K 33/04* (2013.01); *A61K 36/47* (2013.01); *A61K 47/36* (2013.01); *A61P 35/00* (2018.01)

(56) References Cited

FOREIGN PATENT DOCUMENTS

| | | | | |
|---|---|---|---|---|
| WO | WO-0061153 A1 | * | 10/2000 | ............ A61K 31/58 |
| WO | WO-2006061153 A1 | | 6/2006 | |

OTHER PUBLICATIONS

Frank; "Xanthan Gum: A Multifaceted Polysaccharide"; 2015; https://knowledge.ulprospector.com/2099/fbn-xanthan-gum-a-multifaceted-polysaccharide/; accessed Jul. 1, 2022 (Year: 2015).*

Jackson et al.; "Xerosis with Pruritis" abstract; in xPharm: The Comprehensive Pharmacology Reference, 2007; https://www.sciencedirect.com/topics/chemistry/keratolytic; accessed 12/16/202 (Year: 2007).*

Park et al.; "Comparison of Different Gum-Based Thickeners Using a Viscometer and Line Spread Test: A Preliminary Study"; 2014; Ann. Rehabil. Med.; 38(1): 94-100; http://dx.doi.org/10.5535/arm.2014.38.1.94 (Year: 2014).*

Krstonosic et al.; "Influence of xanthan gum on oil-in-water emulsion characteristics stabilized by OSA starch"; 2014; Food Hydrocolloids; 45 (2015): 9-17; http://dx.doi.org/10.1016/j.foodhyd.2014.10.024 (Year: 2014).*

Punjabi et al.; "Solasodine glycoalkaloids: a novel topical therapy for basal cell carcinoma. A double-blind, randomized, placebo-controlled, parallel group, multicenter study"; 2008; International Journal of Dermatology; 47:78-82 (Year: 2008).*

Lanoy et al.; "Skin cancers associated with autoimmune conditions among elderly adults"; 2010; British Journal of Cancer; 103: 112-11 (Year: 2010).*

"International Application Serial No. PCT/AU2017/050188, International Preliminary Report on Patentability mailed Jan. 5, 2008", (Jan. 5, 2018), 129 pgs.

"International Application Serial No. PCT/AU2017/050188, International Search Report mailed May 10, 2017", (May 10, 2017), 4 pgs.

"International Application Serial No. PCT/AU2017/050188, Written Opinion mailed May 10, 2017", (May 10, 2017), 7 pgs.

Cham, B. E., et al., "Topical treatment of malignant and premalignant skin lesions by very low concentrations of a standard mixture (BEC) of solasodine glycosides", Cancer Letters 59.3, (1991), 183-192.

Cham, Bill E., "Solasodine glycosides: a topical therapy for actinic keratosis. a single-blind, randomized, placebo-controlled, parallel group study with CuradermBEC5", Journal of Cancer Therapy 4.2, (2013), 588-596.

Chou, T. C., et al., , Applications of the median-effect principle for the assessment of low-dose risk of carcinogens and for the quantitation of synergism and antagonism of chemotherapeutic agents, New avenues in developmental cancer chemotherapy 8, (1987), 37-64.

Nagourney, R. A., et al., "Ex vivo analysis of topotecan: advancing the application of laboratory-based clinical therapeutics", British journal of cancer 89.9, (2003), 1789.

"Chinese Application No. 2017800219843, Search Report dated Jul. 27, 2020", (Jul. 27, 2020), 3 pgs.

"European Application Serial No. 17759014.8, Extended European Search Report mailed Oct. 2, 2019", (Oct. 2, 2019), 10 pgs.

"Russian Application No. 2018134288, Search Report dated Jul. 27, 2020", (Jul. 27, 2020), 2 pgs.

Tiossi, Renata FJ, et al., "In vitro and in vivo evaluation of the delivery of topical formulations containing glycoalkaloids of Solanum lycocarpum fruits", European Journal of Pharmaceutics and Biopharmaceutics 88.1, (2014), 28-33.

* cited by examiner

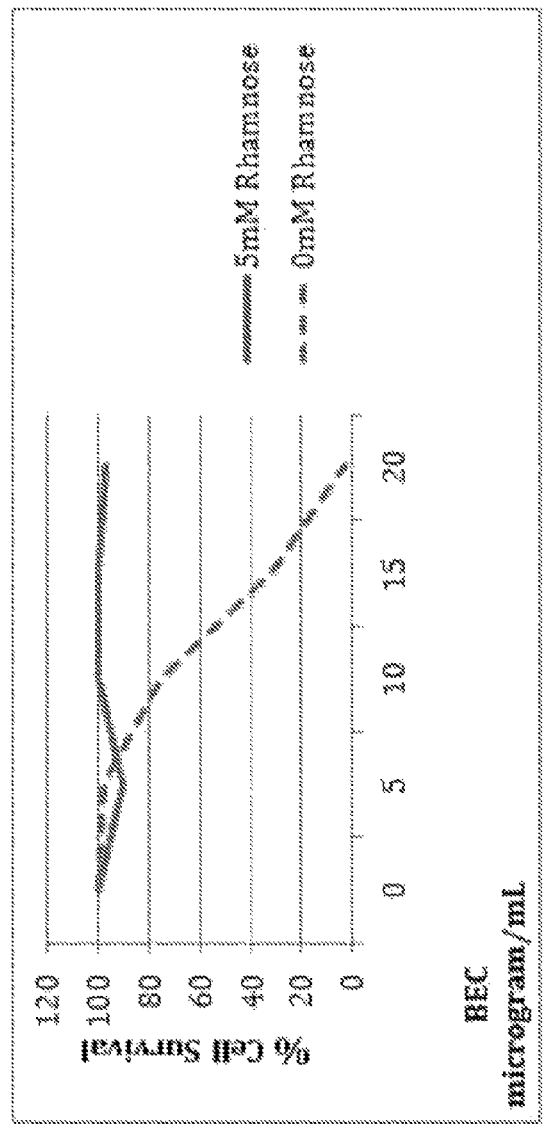

GLYCOALKALOID COMBINATIONS AND VARIOUS USES THEREOF

FIELD OF THE INVENTION

The present invention relates to the use of glycoalkaloids, such as solasonine and solamargine, in treatment of cancer such as skin cancer, and to compositions for use in such treatment. More particularly the present invention relates to providing an improved, substantially stable formulation for the glycoalkaloids which minimises or reduces degradation of these active molecules.

BACKGROUND

Cytotoxic chemotherapy remains one of the premier treatment options to combat cancer. However, the efficacy of chemotherapy is limited by the fact that not all tumours respond optimally. Thus, single-modality chemotherapy with existing drugs is rarely curative. In addition, drug-resistant tumour cells often emerge when a single agent is used. Furthermore, most standard chemotherapies act on all rapidly dividing normal and cancerous cells and were originally identified because they kill cells in general by a process known as indiscriminate cytotoxicity. Consequently, standard chemotherapies are indiscriminate and have a low safety profile.

Apoptosis is a form of cell death in which a programmed sequence of events leads to the elimination of cells without releasing harmful substances into the surrounding area. Apoptosis eliminates old cells, unnecessary cells, and unhealthy cells. Roughly 50 billion cells undergo apoptosis each day in humans. For every normal cell, there is a time to live and a time to die. When apoptosis does not work correctly, cells that should be eliminated may persist and become immortal, for example in cancer. Cancer can start in any place in the body. It starts when cells grow out of control and crowd out normal cells. In cancer cells, the process of apoptosis is defunct but cell division is intact resulting in excessive quantities of cancer cells, which are prone to spreading to other parts of the body (metastasis).

Targeted therapies that induce apoptosis are currently the focus of much anti-cancer drug development. Other targeted therapies may include those which cause cell death by oncosis (ischemic cell death) and/or necrosis.

Thus, substances either singly or by combination that can induce cell death in cancer cells are sought after to treat cancer.

Glycoalkaloids are conjugated forms of steroidal alkaloids which have a sugar moiety bound to the alkaloid moiety. The sugar moiety can be a monosaccharide, disaccharide, oligosaccharide or polysaccharide. Certain glycoalkaloids derived from plants have been observed to be poisonous or have anti-cancer properties.

For example, solasodine [(3β,22α,25R)-Spirosol-5-en-3-ol] is *solanum* type steroid alkaloid chemical compound with a C27 cholestane skeleton that occurs in plants of the Solanaceae family. The chemical structural formula of solasodine is shown below.

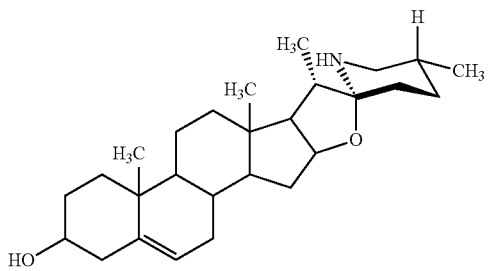

The chemical structure of the steroidal alkaloid Solasodine

Both solasonine [(22R,25R)-spiro-5-en-3β-yl-α-L-rhamnopyranosyl-(1→2 gal)-O-β-D-glucopyranosyl-(1→3 gal)-β-D-galactopyranose] and solamargine [(22R,25R)-spiro-5-en-3β-yl-α-L-rhamnopyranosyl-(1→2glu)-O-α-L-rhamnopyranosyl-(1→4glu)-β-D-gluco-pyranose] are glycoalkaloid conjugates derivatives of solasodine and are composed of solasodine rhamnosides (SRs).

Solasonine is a triglycoside conjugate having a rhamnose, glucose and galactose moieties. Solamargine is also a triglycoside conjugate but it has two rhamnose moieties and one glucose moiety.

In nature, the sugar (i.e., glycosidic) moieties of solasodine-derived glycoalkaloids may consist of mono-, di- and tri-glycosides. A mixture of such naturally occurring solasodine-derived glycoalkaloids has been identified in the fruit of *Solanum Sodomaeum* L. which is a nightshade plant species known as Devil's Apple. This mixture has been extracted from the fruit of the Devil's Apple and has been termed BEC. This mixture of glycoalkaloids consists of 33% being the triglycoside solasonine, 33% being the triglycoside solamargine, and 34% being their corresponding mono- and di-glycosides i.e., mono- and di-glycosides of solasodine. In other words, all the glycosides in the mixture contain the same aglycone, solasodine. Glycoalkaloids from this mixture have been shown to be active against cancer in animals and skin tumours in humans.

SR glycoalkaloids target specific mutant (altered) proteins on a range of cell cancer cells.

BEC® and CORAMSINE® (e.g., Solbec Pharmaceuticals Ltd) are mixtures of solasonine and solamargine with anti-cancer properties. CORAMSINE® is composed of the two solasodine glycoalkaloids solasonine and solamargine at a ratio of 1:1 (w/w) i.e., without mono- and di-glycosides of solasodine that can be found in the BEC® mixture. There is a range of other chemotherapeutic agents available with different modes of action. These include anti-tumour antibiotics, anti-mitotic agents, hormones, anti-angiogenic drugs, cytokines, anti-metabolites and alkylating agents.

There exists a need for new and effective drug combinations that can be used to inhibit the growth of cancer cells or preferably eliminate (e.g., by killing) cancer cells and hence effectively treat cancer. The present invention seeks to improve the effectiveness and/or patient outcomes obtained using CORAMSINE® or BEC® monotherapy through combination therapy with other chemotherapeutic agents e.g., with different mode(s) of action to that of SR glycoalkaloids.

Efficacy of any anti-cancer/tumour agent in treatment of cancer not only depend on the type and/or quantity of the anti-cancer agent used but also on the composition of the therapeutic formulation used. For example, concentrations of any glycoalkaloids necessary to achieve therapeutic efficacy for skin may be in orders of magnitude higher than those that could be observed with the same glycoalkaloids to obtain therapeutic efficacy in cancer cell culture studies. One reason for this is that, in cell culture studies the medium employed would generally be a suspension and in the case of skin cancer on patients, the medium may be more of a semi-solid cream consistency.

It is recognised that with cell culture studies, the contact (bioavailability) of the active ingredient with cancer cells is much higher than in the case of the active ingredient in a cream form with skin cancer cells on the human body.

The present invention therefore seeks to provide glycoalkaloids and formulations thereof for interaction with target cells which may be used to ameliorate the effects of cancer and tumours in mammals and which may at least partially overcome one or more of the above disadvantages or provide the public with a useful alternative.

The conditions of storage of crystalline, semi-crystalline and powdered solasodine rhamnosides have already been addressed (WO 200061153A1). However, the stability of glycoalkaloids in solutions, gels and creams have not been reported.

In the earlier work, it was shown that under normal storage conditions, some degradation of glycoalkaloids in pure or semi-pure crystalline or semi-crystalline form could occur. After storage, free sugars which were formed during storage had to be removed before the stored glycoalkaloids could be used in formulation of therapeutic compositions to avoid reduction in anticancer efficacy. Although the degradation of the antineoplastics were low over a short storage period of the solasodine rhamnosides, a significant decrease in anti-tumour efficacy was observed and was due to free sugars obtained by the segregation of the solasodine rhamnosides.

Accordingly, the present invention also seeks to provide an improved, substantially stable formulation for glycoalkaloid conjugates which reduces degradation of these active molecules when present in the formulation.

SUMMARY OF THE INVENTION

In the work leading to the present invention, the Applicant sought to identify formulations of glycoalkaloid compositions which, for example could be suitable for topical applications for treatment of dermal diseases such as skin cancer and/or skin tumorous growth, and minimize or reduce undesirable hydrolysis of the glycoalkaloids in the formulation resulting in release of free (unconjugated) sugars (such as rhamnose saccharides) from the glycoalkaloids into the formulation. The applicant speculated that such improved formulations would benefit from improved therapeutic efficacy for at least two reasons. First, reduction in hydrolysis of the glycoalkaloid in the formulation may maintain levels or concentrations of the active (non-hydrolysed) glycoalkaloid in the formulation sufficient to achieve therapeutic effect even after extended period of storage of the formulation. And second, minimising or reducing formation of free sugar moieties in the formulation may enhance the therapeutic efficacy of the unhydrolysed glycoalkaloids present in the formulation inter alia by reducing competition of the free sugars for glycoalkaloids receptor binding proteins that may be expressed by diseased cells, thereby minimising or reducing the inhibitory effect the free sugars have on the therapeutic efficacy of non-hydrolysed glycoalkaloids in the formulation.

Furthermore, in the work leading to the present invention, the Applicant sought to identify chemotherapeutic agents that could be used in combination with the glycoalkaloids of the present invention, whereby the combination(s) would result in an advantageous synergistic effect on therapy of one or more cancer(s) or tumorous related ailments. For example, such chemotherapeutic agents may be used as additional components in combination with glycoalkaloids in the therapeutic compositions of the present invention.

Accordingly, in one broad aspect, the present invention provides an improved, substantially stable topical formulation for glycoalkaloid conjugates which minimizes or reduces degradation of these active molecules. The compositions of the invention according to this broad aspect will generally be suitable for administration to patients as a gel or cream and/or will be adapted for topical administration.

Accordingly, in one example the present invention provides a topical composition comprising at least a glycoalkaloid, at least one viscosity modifier and at least one keratolytic agent.

The glycoalkaloid used in the composition of the invention will be selected from the group comprising any glycoalkaloids of formula I:

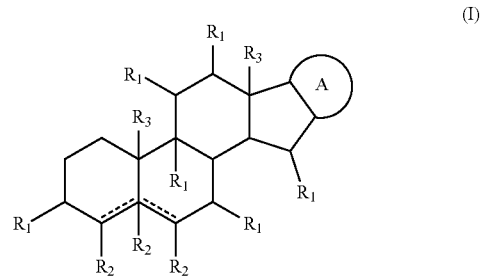

wherein:
each of the dotted lines is separately selected from a single bond and a double bond, such that either both of the dotted lines represent double bonds, or one of the dotted lines represents a double bond and the other dotted line represents a single bond, or both of the dotted lines represent single bonds;

A: represents a radical selected from the following radicals having the general formulae (II) to (V):

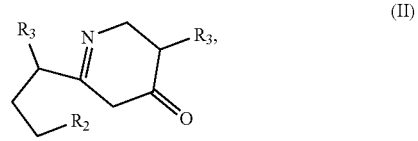

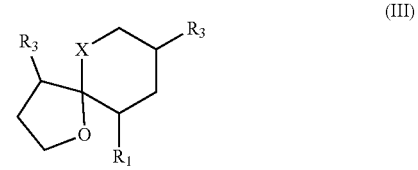

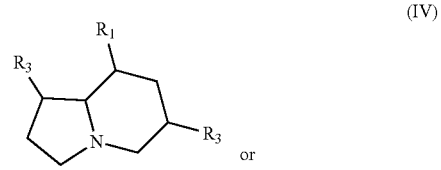

or

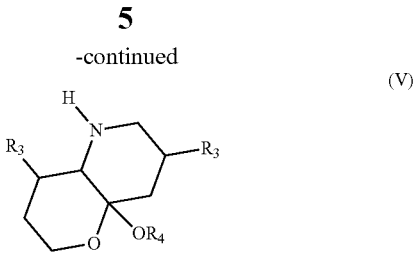

(V)

each of $R_1$ is a radical separately selected from the group consisting of hydrogen, amino, oxo and $OR_4$;

each of $R_2$ is a radical separately selected from the group consisting of hydrogen, amino and $OR_4$ each of $R_3$ is a radical separately selected from the group consisting of hydrogen, alkyl and $R_4$-alkylene;

each of $R_4$ is a radical separately selected from the group consisting of hydrogen, carbohydrate and a carbohydrate derivative;

"X" is a radical selected from the group comprising —$CH_2$—, —O— and —$NH_2$—; and wherein the glycoalkaloid compound includes at least one $R_4$ group in which $R_4$ is a carbohydrate or a derivative thereof selected from the group consisting of: glyceric aldehyde, glycerose, erythrose, threose, ribose, arabinose, xylose, lyxose, altrose, allose, gulose, mannose, glucose, idose, galactose, talose, rhamnose, dihydroxyacetone, erythrulose, ribulose, xylulose, psicose, fructose, sorbose, tagatose, and other hexoses, heptoses, octoses, nanoses, decoses, deoxysugars with branched chains, (e.g., apiose, hamamelose, streptose, cordycepose, mycarose and cladinose), compounds wherein the aldehyde, ketone or hydroxyl groups have been substituted (e.g., N-acetyl, acetyl, methyl, replacement of $CH_2OH$), sugar alcohols, sugar acids, benzimidazoles, the enol salts of the carbohydrates, saccharinic acids, and sugar phosphates.

In one example, the composition may contain a plurality of different glycoalkaloids selected from formula 1. Where the composition only includes a single glycoalkaloid that glycoalkaloid will be present in the composition in a therapeutically effective amount. Where there are multiple glycoalkaloids in the composition, each glycoalkaloid may be present in a sub therapeutic amount but in combination the two or more glycoalkaloids will have a therapeutic effect.

Further the composition may also include a second component in the form of at least one chemotherapeutic agent with a nuclear mechanism of action. Preferably, the second component is a mitotic inhibitor an alkylating agent or an antibiotic.

The viscosity modifier may be any suitable viscosity modifier, or may be a gelling agent and/or viscosity modifier which contain no rhamnose selected from the group consisting of: guar gum, locust bean gum, xanthan gum, gelatin, poloxamer, carbomer and cellulose derivatives. In a preferred embodiment, the at least one viscosity modifier is xanthan gum.

The at least one keratolytic agent may be any suitable keratolytic agent. In one embodiment, the keratolytic agent is selected from the group consisting of: alpha-hydroxy acids selected from: glycolic acid, lactic acid, malic acid, citric acid, and tartaric acid; beta hydroxy acids selected from: salicylic acid, 3-hydroxypropionic acid, beta-hydroxybutyric acid, beta-hydroxy beta-methylbutyrate and carnitine; azelaic acid, benzoyl peroxide, urea, trichloroacetic acid (TCA), carbolic acid (Phenol), croton oil, acetone and sulphur. In a preferred embodiment, the at least one keratolytic agent is selected from the group consisting of: lactic acid, salicylic acid and urea. In another embodiment, the composition comprises a keratolytic agent comprising at least one alpha-hydroxy acid as described herein and may further comprise a keratolytic agent comprising at least one beta-hydroxy acid as described herein. For example, the composition may comprise lactic acid, salicylic acid and urea.

For example, in use, the composition may be comprised of w/w xanthan gum about 0.2-2%, lactic acid about 5-10%, salicylic acid about 5-10% and urea about 3-5%. In an alternate embodiment, the composition may comprise w/w xanthan gum about 1%, lactic acid about 10%, salicylic acid about 10% and urea about 5%.

In one embodiment, the composition is a gel or cream and/or is for topical administration.

In another embodiment, the composition is essentially without free saccharides of the type which may inhibit an interaction between the glycoalkaloids and their target cell. For example, the composition is essentially devoid of free rhamnose saccharides or rhamnose like molecules.

As used herein the term "free saccharide" will be understood to refer to any saccharide such as a mono-, di-, tri-, oligo- or poly-saccharide, or derivative thereof, which is not bound to an alkaloid.

In a second broad aspect, the present invention provides method of preparing or manufacturing a topical composition as described herein according to the first broad aspect. The method may comprise combining and/or admixing and/or dissolving a therapeutically effective amount of the glycoalkaloid or a plurality of different glycoalkaloids e.g., wherein each glycoalkaloid is selected from the group of glycoalkaloids of formula I described herein above, with an amount of the at least one viscosity, and an amount of the at least one keratolytic agent. For example, where the method includes combining and/or admixing and/or dissolving only a single glycoalkaloid that glycoalkaloid will be combined and/or admixed and/or dissolved in a therapeutically effective amount. Alternatively, where multiple different glycoalkaloids are being combined and/or admixed and/or dissolved to prepare the composition, each of the different types of glycoalkaloids may be combined and/or admixed and/or dissolved in a sub therapeutic amount but in combination the two or more different glycoalkaloids will have a therapeutic effect.

For example, the method according to this aspect comprises dissolving, combining and/or admixing a glycoalkaloid in a pharmaceutically acceptable carrier, diluent and/or excipient suitable for topical delivery of the composition. For example, the carrier, diluent and/or excipient may be aqueous or non-aqueous. In one such example, the pharmaceutically acceptable carrier, excipient and/or diluent comprises any one or both of said at least one viscosity modifier and said at least one keratolytic agent.

In one embodiment, the method of preparing a topical composition according to this aspect may further comprise combining and/or admixing and/or dissolving a second component in the form of at least one chemotherapeutic agent with a nuclear mechanism of action.

In another embodiment, the method of preparing a topical composition according to this aspect, may further comprise removing, e.g., from any resulting combination or admixture or composition, free saccharides which may inhibit an interaction between the glycoalkaloids and their target cell. For example, the method may comprise removing from any resulting combination or admixture or composition free rhamnose saccharides or rhamnose like molecules.

In a third broad aspect, the present invention provides a topical composition when prepared by performing the method according to this second broad aspect described herein above.

In a fourth broad aspect, the present invention also provides a method for treating a tumorous growth comprising the step of administering a therapeutically effective synergistic amount of a composition described herein.

In a fifth broad aspect, the present invention further provides a method of treating a patient having or suffering from a dermal disease associated with cancer, viral infections, bacterial infections, parasitic infections, fungal infections, inflammatory diseases and/or psoriasis. The method comprises administering topically to the patient a therapeutically effective amount of the topical composition according to any aspect of the invention described herein.

In one embodiment, the administration step comprises applying the therapeutically effective amount of said composition to the disease state in the patient. For example, the method comprises applying topically the composition to the skin of the patient. In one such example, the patient has or suffers from a skin cancer and/or a skin tumour, and said method comprises topically applying a therapeutically effective amount of the composition to an area of the skin of patient which comprises the skin cancer and/or skin tumour. In another example, the patient has or suffers from dermal disease associated viral infections, bacterial infections, parasitic infections, fungal infections, inflammatory diseases and/or psoriasis, and said method comprises topically applying a therapeutically effective amount of the composition to an area of the skin of patient comprising infected, inflamed and/or damaged skin cells as a result of the infection, inflammatory diseases and/or psoriasis. Preferably, the patient is a human.

It will be understood that the term "patient" as used herein, according to any aspect, embodiment and/or example of the invention described hereof includes a human subject.

In a sixth broad aspect, the present invention further provides use of the topical composition according to any aspect described herein in treating topically a dermal disease associated with cancer, viral infections, bacterial infections, parasitic infections, fungal infections, inflammatory diseases and/or psoriasis.

In a seventh broad aspect, the present invention also provides use of the composition according to any aspect described herein in the manufacture of a topical medicament for treating topically a dermal disease associated with cancer, viral infections, bacterial infections, parasitic infections, fungal infections, inflammatory diseases and/or psoriasis.

In an eighth broad aspect, the present invention further provides use of at least a glycoalkaloid, at least one viscosity modifier and at least one keratolytic agent in the manufacture of a topical medicament for the treatment of a dermal disease associated with cancer, viral infections, bacterial infections, parasitic infections, fungal infections, inflammatory diseases and/or psoriasis. In one example, the medicament is formulated for topical administration to the skin of a human patient having or suffering from said dermal disease. For example, the medicament is for treatment a skin cancer and/or a skin tumour in a patient and the medicament is formulated for application to an area of the skin of the patient which comprises the skin cancer and/or skin tumour.

In one embodiment the glycoalkaloid used in the medicament is selected from the group comprising glycoalkaloids of formula I:

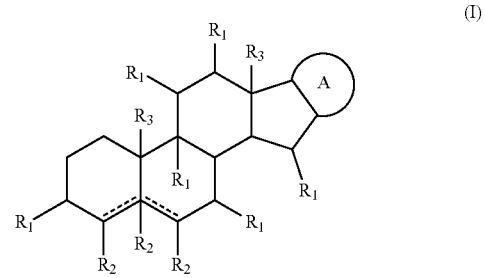

wherein:
each of the dotted lines is separately selected from a single bond and a double bond, such that either both of the dotted lines represent double bonds, or one of the dotted lines represents a double bond and the other dotted line represents a single bond, or both of the dotted lines represent single bonds;

A: represents a radical selected from the following radicals having the general formulae (II) to (V):

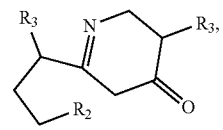

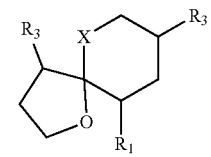

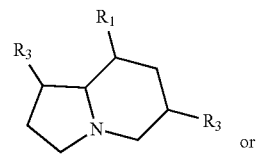

or

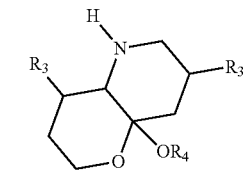

each of $R_1$ is a radical separately selected from the group consisting of hydrogen, amino, oxo and $OR_4$;
each of $R_2$ is a radical separately selected from the group consisting of hydrogen, amino and $OR_4$;
each of $R_3$ is a radical separately selected from the group consisting of hydrogen, alkyl and $R_4$-alkylene;
each of $R_4$ is a radical separately selected from the group consisting of hydrogen, carbohydrate and a carbohydrate derivative;
"X" is a radical selected from the group comprising —$CH_2$—, —O— and —$NH_2$—; and wherein the glycoalkaloid compound includes at least one $R_4$ group in which $R_4$ is a carbohydrate or a derivative thereof selected from the group consisting of glyceric aldehyde, glycerose, erythrose, threose, ribose, arabinose, xylose, lyxose, altrose, allose, gulose, mannose, glucose, idose, galactose, talose, rhamnose, dihydroxyacetone, erythrulose, ribulose, xylulose, psicose, fructose, sorbose, tagatose, and other hexoses, heptoses, octoses, nanoses, decoses, deoxysugars with branched chains, (e.g., apiose, hamamelose, streptose, cordycepose, mycarose and cladinose), compounds wherein the aldehyde, ketone or hydroxyl groups have been substituted (e.g., N-acetyl, acetyl, methyl, replacement of $CH_2OH$), sugar alcohols, sugar acids, benzimidazoles, the enol salts of the carbohydrates, saccharinic acids, and sugar phosphates.

In one embodiment, the medicament comprises a plurality of glycoalkaloids selected from formula I.

In another embodiment, the medicament comprises a second component in the form of at least one chemotherapeutic agent with a nuclear mechanism of action.

In another embodiment according to this aspect, the viscosity modifier is selected from the group consisting of: guar gum, locust bean gum, xanthan gum, gelatin, poloxamer, carbomer and cellulose derivatives. For example, the viscosity modifier is xanthan gum.

In another embodiment according to this aspect, the keratolytic agent is selected from the group consisting of: alpha-hydroxy acids selected from: glycolic acid, lactic acid, malic acid, citric acid, and tartaric acid; beta hydroxy acids selected from: salicylic acid, 3-hydroxypropionic acid, beta-hydroxybutyric acid, beta-hydroxy beta-methylbutyrate and carnitine; azelaic acid, benzoyl peroxide, urea, trichloroacetic acid (TCA), carbolic acid (Phenol), croton oil, acetone and sulphur. For example, the composition comprises a keratolytic agent comprising at least one alpha-hydroxy acid as described herein and may further comprise a keratolytic agent comprising at least one beta-hydroxy acid as described herein. For example, the keratolytic agent is selected from the group consisting of: lactic acid, salicylic acid and urea. In one example, the composition may comprise lactic acid, salicylic acid and urea.

In another embodiment according to this aspect, the medicament includes by w/w xanthan gum about 0.2-2%, lactic acid about 5-10%, salicylic acid about 5-10% and urea about 3-5%.

In another embodiment according to this aspect, the medicament includes by w/w xanthan gum about 1%, lactic acid about 10%, salicylic acid about 10% and urea about 5%.

In yet another embodiment according to this aspect, the medicament is formulated as a gel or cream and/or is for topical administration.

In yet another embodiment according to this aspect, the medicament is essentially without free saccharides of the type which inhibit an interaction between the glycoalkaloids and their target cell. For example, the medicament is essentially devoid of free rhamnose saccharides or rhamnose like molecules.

BRIEF DESCRIPTION OF THE DRAWINGS

FIG. 1, is a graphic representation showing the effect of addition of free rhamnose (5 mM) and increasing concentrations (0, 5, 10, 15 and 20 µM) of BEC extract formulation on percentage survival of malignant melanoma cells. Free rhamnose exerts a protective effect against the efficacy of the anticancer BEC compounds.

DETAILED DESCRIPTION OF THE INVENTION

General

Those skilled in the art will appreciate that the invention described herein is susceptible to variations and modifications other than those specifically described without departing from the spirit and scope thereof. The invention includes all such variations and modifications. The invention also includes all of the steps, features, compositions, components, aspects, examples and embodiments referred to or indicated in the specification, individually or collectively, and any and all combinations or any two or more of said steps or features.

Each document, reference, patent application or patent cited in this text herein, whether supra or infra, is expressly incorporated herein in its entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific aspects, embodiments or examples described herein, which are intended for the purpose of exemplification only. Functionally equivalent products, compositions of matter, formulations and methods are clearly within the scope of the invention as described herein.

Definitions for selected terms used herein may be found within the detailed description of the invention and apply throughout. Unless otherwise defined, all other scientific and technical terms used herein have the same meaning as commonly understood to one of ordinary skill in the art to which the invention belongs.

Each example, embodiment and aspect described herein is to be applied mutatis mutandis to each and every other example, embodiment and aspect unless specifically stated otherwise.

Definitions

Throughout the specification and claims, unless the context requires otherwise, the word "comprise" or variations such as "comprising" will be understood to imply the inclusion of a stated step or element or integer or group of steps or elements or integers but not the exclusion of any other step or element or integer or group of steps or elements or integers. It will be appreciated that modifications and changes may be made to the embodiments described therein without departing from the spirit and scope of the invention as herein described.

Throughout this specification, unless stated otherwise or the context requires otherwise, reference to a single step, composition or matter, group of steps or group of compositions of matter shall be taken to encompass one and a plurality (i.e., one or more) or those steps, compositions or matter, group of steps or group of compositions of matter. It must be noted that, as used herein and in the appended claims, the singular forms "a," "or," and "the" include plural references unless the context clearly dictates otherwise. Thus, for example, reference to "glycoalkaloid" or "glycoalkaloid conjugate" or "solasodine conjugate" includes a plurality of such glycoalkaloids, glycoalkaloid conjugates or solasodine conjugates, and so forth.

The term "substantially stable" as used throughout this specification in reference to stability of the compositions, formulations and medicaments of the present invention would be understood to mean that a proportion or concentration of at least about 70%, 75%, 80%, 85%, 90%, 91%, 92%, 93%, 94%, 95%, 96%, 97%, 98%, or 99% of the described active ingredient(s) in the formulation or composition or medicament retain their structural integrity and remain unhydrolysed or non-degraded in the formulation or composition or medicaments relative to the proportion or concentration or the of the described active ingredient(s) when formulated after at least 3 months, more preferably 4, 5, 6, 7, 8, 9, 10, 11, 12, 13, 14, 15, 16, 17, 18 months or at least 2 years or at least 3 years or at least 4 years. In certain embodiments, a substantially stable composition or formulation is one where a concentration or proportion of at least about 90% of the described active ingredient(s) in the formulation or composition or medicament remains unhydrolysed or non-degraded in the formulation or composition or medicament relative to the concentration proportion of the active ingredient when formulated, after at least 6, 7, 8, 9, 10, 11, 12, 13, 14, 15, 16, 17, 18 months or at least 2 years or at least 4 years.

For example, the concentration or proportion of the described active ingredient(s) in the formulation or composition or medicament that remains unhydrolysed or non-degraded in the formulation or composition or medicament is determined after storage of the formulation or composition or medicament at room temperature or 25° C. and optionally at 60% relative humidity for at least 6, 7, 8, 9, 10, 11, 12, 13, 14, 15, 16, 17, 18 months or at least 2 years or at least 4 years from the time of manufacture of formulation or composition or medicament.

For example, a "substantially stable" composition, formulation and medicament of the present invention will be understood to include those compositions, formulations and medicaments whereby a proportion or concentration of about 70%, 75%, 80%, 85%, 90%, 91%, 92%, 93%, 94%, 95%, 96%, 97%, 98% or 99% of the glycoalkaloids included in the formulations, compositions or medicaments remain in their conjugates form so as to not be hydrolysed or broken down or degraded into their respective solasodine aglycone and free sugar(s) moieties (i.e., at least about 70%, 75%, 80%, 85%, 90%, 91%, 92%, 93%, 94%, 95%, 96%, 97%, 98% or 99% of the glycoalkaloids have not been broken down to release free saccharides such as free rhamnose saccharides or rhamnose like molecules) after at least 3 months, more preferably 4, 5, 6, 7, 8, 9, 10, 11, 12, 13, 14, 15, 16, 17, 18 months or at least 2 years or at least 3 years or at least 4 years. In certain examples, a concentration or proportion of at least about 90% of the glycoalkaloids included in the formulations, compositions or medicaments remain in their conjugates form after at least 3 months, more preferably 4, 5, 6, 7, 8, 9, 10, 11, 12, 13, 14, 15, 16, 17, 18 months or at least 2 years or at least 3 years or at least 4 years. For example, the proportion or concentration of glycoalkaloids that remain in their conjugates form is determined after storage of the composition, formulation or medicament at room temperature or 25° C. for the above specified duration.

Alternatively or in addition, the term "substantially stable" when referring to a composition, formulation and medicament of the present invention would be understood to encompass those compositions, formulations and medicaments which are essentially devoid of free saccharides of the type which inhibit an interaction between the glycoalkaloids and their target cell such as free rhamnose saccharides or rhamnose like molecules. For example, the medicament is essentially devoid of free rhamnose saccharides or rhamnose like molecules.

As used herein throughout this specification the term "derivative" or "derived from" shall be taken to indicate that a specified integer may be obtained from a particular source albeit not necessarily from that source.

To simplify the description of the invention, the terms "glycoalkaloid", "solasodine conjugate" and "solasodine rhamnoside (SR)" and are intended to be used interchangeably. They are used herein to include any compound that comprises a solasodine molecule and at least one rhamnose residue.

The term "rhamnose" in intended to mean a deoxy sugar based on a saccharide of the general formula $C_6H_{12}O_5$. For the purposes of the present description and claims, unless expressly stated otherwise the term "rhamnose" is intended to include a rhamnose of the formula $C_6H_{12}O_5$ as well as functional derivatives thereof.

The term "substituted rhamnose" is intended to mean a rhamnose residue which has had at least one hydroxyl group substituted with at least one alkyl group. For example, a hydroxyl group may have been substituted with a methyl group. The term "substituted solasodine rhamnoside" is intended to mean a solasodine conjugate of the invention comprising at least one substituted rhamnose.

To simplify the description of the invention, the terms "carbohydrate" and "saccharide" will be used herein to include any compound that could be reasonably construed to comprise the empirical formula $C_nH_{2n}O_n$ (wherein n is a positive number). They are intended to include monosaccharides, disaccharides, oligosaccharides, and polysaccharides, such as sugars, starch, and cellulose etc.

The term "viscosity modifier" is intended to mean any agent which is capable of adjusting, effecting or controlling the viscosity of a substance such as (but not limited to) a liquid, cream or gel. The term "viscosity" is intended to correspond to the informal concept of "thickness".

In the present specification and claims, the term "free saccharide" refers to any saccharide such as a mono-, di-, tri-, oligo- or poly-saccharide, or derivative thereof, which is not bound to an alkaloid.

Specific

In the inventor's earlier work discussed in WO 2000061153A1, it was reported that free sugars (sugars unconjugated to a glycoalkaloid) in extracted semi crystalline BEC glycoalkaloids preparations had to be removed from the preparations prior to inclusion into anticancer effective formulations. This was necessary inter alia because during storage of the semi crystalline BEC preparations some hydrolysis of the glycoalkaloids occurred which resulted in release of free rhamnose moieties. This meant that (i) the active glycoalkaloid compounds (i.e., active glycoalkaloid molecules were available), and (ii) the free rhamnose interfered with the anticancer efficacy of the remaining non-hydrolysed glycoalkaloids.

It is unknown how the washed BEC semi crystalline preparations containing no free sugars behave when incorporated in formulation such as for example, formulations for topical administration such as creams or gels, for anti-cancer and/or other therapeutic uses.

The Applicant's data presented in the working examples that follow demonstrates that in therapeutic compositions of glycoalkaloids, such as compositions formulated for topical administration (e.g., creams) it is also most desirable to prevent hydrolysis of the glycoalkaloids and release of free sugars (such as rhamnose) in those formulations.

Accordingly, based on the Applicant's work presented herein, the Applicant reasoned that, for example, when referring to use of topical formulations (e.g., creams or gels) in therapy of skin cancers and/or skin tumours, specific ingredients that, on their own, improve the anti-cancer efficacy of glycoalkaloids in the topical formulations as well as prevent the breakdown and stabilize the anti-cancer activity of the glycoalkaloids would be most beneficial for inclusion in such formulations so as to achieve an improved and effective treatment of skin cancers and/or skin tumours e.g., in a clinically timely period.

Accordingly, based on the work presented herein, the Applicant concluded that there are two requirements for achieving a therapeutically effective formulation such as a topical formulation (e.g., cream) of glycoalkaloids. First, the formulation would need to reduce or minimise hydrolysis of the therapeutically active glycoalkaloids in the formulation so as to retain the active glycoalkaloids at the appropriate therapeutically effective (e.g., anticancer) amounts or concentration in the formulation. Second, the formulation would need to reduce or minimise or abolish the release of free sugars such as free rhamnose (i.e., by hydrolysis of the glycoalkaloids), as the free sugars such as rhamnose competes with the non-hydrolysed glycoalkaloids for receptors on the disease cells (e.g., cancer or tumour cells), thereby inhibiting the therapeutic efficacy of the glycoalkaloids when the formulation is administered to the patient or comes into contact with the disease cells (e.g., cancer or tumour cells).

The results presented in the working examples that follow, demonstrate that free rhamnose sugar moieties (e.g., which may be present in an anticancer formulation of glycoalkaloids) interfere with the binding of glycoalkaloids to rhamnose binding proteins (RBPs), initially described as endogenous endocytic lectins (EELs). RBPs are mutant proteins that have previously been shown to be present on the surface of certain cancer cells. Normal, non-cancer, cells may lack RBP or contain much less than are present on cancer cells. Without being bound by any theory or specific mode of action, the Applicant believes that solasodine rhamnoside (SR) glycoalkaloids of the present invention specifically bind to the RBPs on the cancer cells, which result in internalisation of the SR glycoalkaloids into the cancer cells. Once internalised in the cancer cell, the solasodine moiety of the SR then expresses its antineoplastic activity to initiate death of the cancer cells e.g., by apoptosis, ischemic cell death (also known to as oncosis) or necrosis mediated pathways. Accordingly, the Applicant considers that anticancer drug development that targets RBP receptors can drive cancer therapy.

Accordingly, in the work leading to the present invention the Applicant has speculated that the SR glycoalkaloids of the present invention can be employed e.g., as targeted anti-cancer and/or anti-tumour therapy for cancer and/or tumour cells with RBP receptors. In the work leading to the present invention, the Applicant further speculated that the SR glycoalkaloids of the present invention have anti-cancer mode of action which is different to currently used chemotherapeutic agents such as anti-tumour antibiotics, anti-mitotic agents, hormones, anti-angiogenic drugs, cytokines, anti-metabolites and alkylating agents. As such, the Applicant speculated that the glycoalkaloids of the present invention can be used inter alia as monotherapies against cancer or in combination with the above anti-tumour agents.

Accordingly, in one example, the present invention resides in a topical composition comprising at least a glycoalkaloid, at least one viscosity modifier and at least one keratolytic agent. More particularly the present invention for example provides an improved, substantially stable topical formulation for glycoalkaloid conjugates which minimizes or reduces degradation of these glycoalkaloid active molecules. The compositions of the invention will generally be suitable for administration to patients as a gel or cream and/or will be adapted for topical administration.

The glycoalkaloid used in the composition of the invention will be selected from the group comprising any glycoalkaloids of formula I:

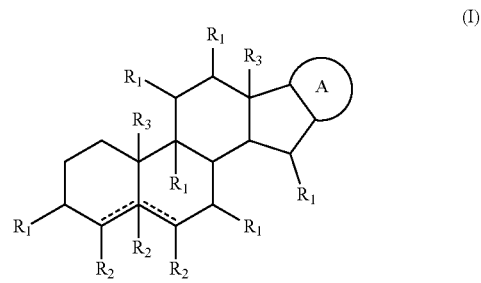

wherein:
each of the dotted lines is separately a single bond or a double bond, such that either both of the dotted lines represent double bonds, or one of the dotted lines represents a double bond and the other dotted line represents a single bond, or both of the dotted lines represent single bonds;

A: represents a radical selected from the following radicals having the general formulae (II) to (V):

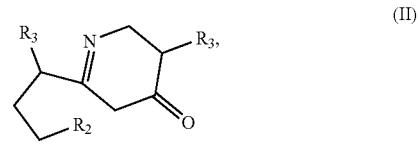

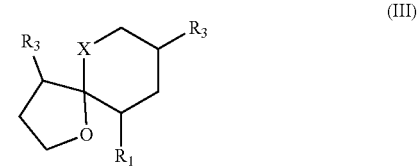

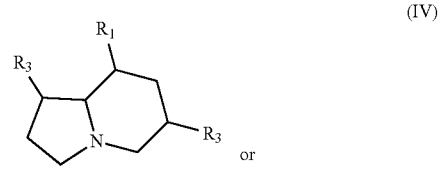

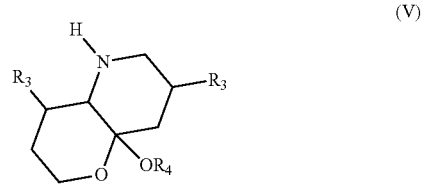

each of $R_1$ is a radical separately selected from the group consisting of hydrogen, amino, oxo and $OR_4OR^4$;
each of $R_2$ is a radical separately selected from the group consisting of hydrogen, amino and $OR_4$;
each of $R_3$ is a radical separately selected from the group consisting of hydrogen, alkyl and $R^4$-alkylene;
each of $R_4$ is a radical separately selected from the group consisting of hydrogen, carbohydrate and a carbohydrate derivative;

"X" is a radical selected from the group comprising —CH$_2$—, —O— and —NH$_2$—; and wherein the glycoalkaloid compound includes at least one R$_4$ group in which R$_4$ is a carbohydrate or a derivative thereof selected from the group comprising glyceric aldehyde, glycerose, erythrose, threose, ribose, arabinose, xylose, lyxose, altrose, allose, gulose, mannose, glucose, idose, galactose, talose, rhamnose, dihydroxyactone, erythrulose, ribulose, xylulose, psicose, fructose, sorbose, tagatose, and other hexoses, heptoses, octoses, nanoses, decoses, deoxysugars with branched chains, (e.g., apiose, hamamelose, streptose, cordycepose, mycarose and cladinose), compounds wherein the aldehyde, ketone or hydroxyl groups have been substituted (e.g. N-acetyl, acetyl, methyl, replacement of CH$_2$OH), sugar alcohols, sugar acids, benzimidazoles, the enol salts of the carbohydrates, saccharinic acids, and sugar phosphates.

In accordance with this example, the composition may contain a plurality of different glycoalkaloids selected from formula I. Where the composition only includes a single glycoalkaloid that glycoalkaloid will be present in the composition in a therapeutically effective amount. Where there are multiple glycoalkaloids in the composition, each glycoalkaloid may be present in a sub therapeutic amount but in combination the two or more glycoalkaloids will have a therapeutic effect.

The glycoalkaloids used in the composition may be varied. Preferably, the glycoalkaloids are triglycoside glycoalkaloids, solasodine glycosides or are selected from the group of glycoalkaloids consisting of: solamargine, solasonine, solanine, tomatine, solanocapsine and 26-aminofurostane.

The glycoalkaloids may be chiral, stereoisomers and mixtures thereof including enantiomers and/or diastereoisomers. Furthermore, the glycoalkaloids may be obtained from natural sources, synthesized or produced by chemically modifying other glycoalkaloids.

The number of glycoalkaloids used may be varied, as may their relative ratios in the composition. However, when the composition comprises two glycoalkaloids they may be present in a ratio selected from the group of ratios consisting of approximately: 1:6-1:0.5; 1:5; 1:4; 1:3; 1:2, 1:1.5 and 1:1.

Preferably, the glycoalkaloids are solamargine and solasonine in a ratio between about 1:6 and 6:1 or more preferably in a ratio between about 1:4 and 4:1, 1:3 and 3:1 or 1:2 to 2:1.

When the glycoalkaloids are solamargine and solasonine and they are present in a 1:1 ratio it is preferred that the glycoalkaloids are isolated. Alternatively, when the glycoalkaloids are solasonine and solamargine it is preferred that they do not constitute less than 66% of glycosides in the composition. In one embodiment according to this example, the glycoalkaloid composition comprises a proportion of 33% solasonine, 33% solamargine, and 34% their corresponding mono- and di-glycosides in which the aglycone is solasodine. In one embodiment according to this example, the glycoalkaloid composition is BEC™ or CORAMSINE® (e.g., Solbec Pharmaceuticals Ltd).

In a preferred form of the invention, the glycoalkaloid composition is essentially free of late-eluting degradants.

Preferably, the glycoalkaloids constitute a proportion greater than 70%-90% of the glycosides in the composition, more preferably 91-95% and even more preferably 96-100% of the glycosides in the composition.

The amount of glycoalkaloids in the compositions of the present invention may be varied depending on their intended end use. Preferably, the compositions comprise about 0.001%-5% or 10% glycoalkaloids, more preferably 0.01%-5% or 10% and even more preferably 0.1%-5% or 10% glycoalkaloids.

The actual concentration of glycoalkaloids in the composition may vary and depend at least on the nature of the ailment being treated and the condition of the subject to be treated. Skilled practitioners can determine the most appropriate dose using their ordinary skill and taking into account various parameters that apply in such situations. For example, when the ailment is a tumorous growth the higher the cancer load in a particular patient the higher the dose of glycoalkaloids that can be administered and well tolerated by the patient. Preferably, the concentration of glycoalkaloids administered as part of the combination therapy is less than in a comparable situation in which it was to be administered as a monotherapy. The amount or concentration (w/w) of glycoalkaloid in the final composition may be about 0.1 mg/kg-100 mg/kg, 1 mg/kg-80 mg/kg, 5 mg/kg-60 mg/kg or 10 mg/kg-40 mg/kg or 0.5-5 mg/kg or 0.75-4 mg/kg or 1-3 mg/kg. Preferably the amount or concentration (w/w) of glycoalkaloid in the final composition is about 0.5-5 mg/kg, 0.75-4 mg/kg or 1-3 mg/kg. In one example the composition is a cream formulation comprising 0.005% (w/w) glycoalkaloids.

The composition may also include a second component in the form of at least one therapeutic agent suitable for treating cancer, viral infections, bacterial infections, parasitic infections, fungal infections, inflammatory diseases, and/or psoriasis.

To the extent that the composition is used to treat a tumorous ailment the composition may also include a second component in the form of at least one chemotherapeutic agent with a nuclear mechanism of action. For the purposes of the present invention "nuclear mechanism of action" means that the chemotherapeutic agent acts within, at or near the nucleus of the cancer cell. For example, the agent may interfere with mitosis by inhibiting the formation of, binding to or otherwise disrupting the function of one or more proteins or structures involved in mitosis such as tubulin, microtubules, centrioles or spindles. Alternatively, or in addition, the agent may act on or near nucleic acids in the nucleus by damaging, breaking, crosslinking or binding to nucleic acids or otherwise disrupting the function of DNA or RNA e.g. inhibiting or otherwise interfering with transcription and/or translation. Alternatively, or in addition, the agent may act on one or more enzymes or cofactors associated with DNA structure e.g. the agent may act on topoisomerases, thereby preventing DNA from adopting the appropriate coiled structure.

The composition may also include a second component in the form of at least one chemotherapeutic agent with a nuclear mechanism of action. Preferably, the second component is a mitotic inhibitor an alkylating agent or an antibiotic.

When the second component is a mitotic inhibitor it may be a plant alkaloid such as an alkaloid selected from the group consisting of: vinca alkaloids, taxanes, podophyllotoxins and camptothecan analogs. In one particular form of the invention the second component is vinorelbine, vinorelbine tartrate or paclitaxel or a functional equivalent thereof.

When the second component is an alkylating agent it may be selected from the group consisting of: metal salts, nitrosureas, mustard gas derivatives, ethylenimines, alkylsulfonates, hydrazines and triazines. In one particular form of the invention the second component is mechlorethamine or dacarbazine or a functional equivalent thereof.

When the second component is an antibiotic it may be selected from the group consisting of: anthracyclines and chromomycins. In one particular form of the invention the second component is doxorubicin or a functional equivalent thereof.

In one desired example, the second component comprises at least one chemotherapeutic agent with a nuclear mechanism of action selected from the group: doxorubicin, nitrogen mustard, topotecan and gemcitabine, 5-fluorouracil, CAMP, oxaliplatin, mitomycin C, taxol, trimetrexate, topotecan, 5-fluorouracil combined with oxaliplatin, and 5-flurorouracil combined with CAMP, cisplatin, gemcitabine, iressa, navalbine, taxol, trimetrexate, and topotecan, carmustine, cisplatin, dacarbazine, navalbine, nitrogen mustard, taxol, and temozolomide.

For the purpose of the present invention "functional equivalents" are structurally and/or functionally related compounds that are expected to have similar advantageous effects to the named compound when used in combination with the glycoalkaloid compounds described herein.

Viscosity Modifier

The term "viscosity modifier" is intended to mean any agent which is capable of adjusting, effecting or controlling the viscosity of a substance such as (but not limited to) a liquid, cream or gel. The term "viscosity" is intended to correspond to the informal concept of "thickness".

The viscosity modifier may be any suitable viscosity modifier, or may be a gelling agent and/or viscosity modifier which contain no rhamnose selected from the group consisting of: guar gum, locust bean gum, xanthan gum, gelatin, poloxamer, carbomers and cellulose derivatives.

In one embodiment, the gelling agent or viscosity modifier is xanthan gum.

Xanthan gum is a substance produced by bacterial fermentation or synthetically, and used in foods as a gelling agent and thickener. It is a polysaccharide composed of glucose, mannose, and glucuronic acid.

Keratolytic Agents

Keratolytic agents play an important role in many cream formulations. They are used to exfoliate the skin by causing the outer layer of the skin to loosen and shed.

The at least one keratolytic agent may be any suitable keratolytic agent. In one embodiment, the keratolytic agent is selected from the group consisting of: alpha-hydroxy acids selected from: glycolic acid, lactic acid, malic acid, citric acid, and tartaric acid; beta hydroxy acids selected from: salicylic acid, 3-hydroxypropionic acid, beta-hydroxybutyric acid, beta-hydroxy beta-methylbutyrate and carnitine; azelaic acid, benzoyl peroxide, urea, trichloroacetic acid (TCA), carbolic acid (Phenol), croton oil, acetone and sulphur. The composition may comprise a keratolytic agent comprising at least one alpha-hydroxy acid as described herein and may further comprise at least one keratolytic agent comprising at least one beta-hydroxy acid as described herein.

In a preferred embodiment, the at least one keratolytic agent is selected from the group consisting of: lactic acid, salicylic acid and urea. For example, the composition may comprise lactic acid, salicylic acid and urea.

In one embodiment, the keratolytic agent is the beta-hydroxy acid salicylic acid. Salicylic acid works on the skin by increasing the amount of moisture in the skin and dissolving the substance that causes the skin to stick together (catherins). This makes it easier to shed the skin cells and mimics a cell suspension.

In one embodiment, the keratolytic agent is urea. Urea increases moisture in the skin by softening/dissolving the horny substance (keratin) holding the top layer of skin cells together. This effect helps the dead skin cells, including the dead cancer cells caused by the glycoalkaloids, to fall off and helps the skin retain moisture.

Medicaments of the invention suitable for use in animals and in particular in man, typically must be substantially stable under the conditions of manufacture and storage. The medicaments of the invention comprising the solasodine rhamnosides can be formulated as a solid, a solution, a micro emulsion, a liposome, or other ordered structures suitable to high drug concentration.

Actual dosage levels of the solasodine rhamnosides in the medicament of the invention may be varied in accordance with the nature of the biologically active material, as well as the potential increased efficacy due to the advantages of providing and administering the solasodine rhamnosides (e.g., increased solubility).

As used herein "therapeutically effective amount" will refer to an amount of glycoalkaloid or an amount of the therapeutic composition, formulation or medicament of the present invention comprising glycoalkaloid required to effect a therapeutic response in a human or an animal subject. Amounts effective for such a use will depend on: the desired therapeutic effect; the route of administration; the potency of the solasodine rhamnosides; the desired duration of treatment; the stage and severity of the disease being treated; the weight and general state of health of the patient; and the judgment of the prescribing physician.

In one embodiment, the solasodine rhamnosides, may be combined into a medicament with another biologically active material.

For example, in use, the composition may be comprised of w/w xanthan gum 0.2-2%, lactic acid 5-10%, salicylic acid 5-10% and urea 3-5%. In an alternate embodiment, the composition may comprise w/w xanthan gum 1%, lactic acid 10%, salicylic acid 10% and urea 5%.

In one embodiment, the composition is a gel or cream and/or is for topical administration.

In one example, the composition is a cream comprising one or more of emulsifying wax, white soft paraffin, liquid paraffin, propylene glycol and water e.g., as the cream base. Optionally, the cream composition may further comprise chlorocresol.

In a second embodiment, the composition is essentially without free saccharides of the type which may inhibit an interaction between the glycoalkaloids and their target cell.

In a preferred form of the invention, the composition is essentially free of saccharides. In particular, the term "free saccharide" refers to any saccharide such as a mono-, di-, tri-, oligo- or poly-saccharide, or derivative thereof, which is not bound to an alkaloid. In a highly preferred form of the invention, the composition is free of rhamnose or rhamnose like molecules.

Without being bound by any specific theory or particular mode of action the inventor has speculated that in case of topical compositions of the present invention when used to treat dermal cancer or tumors the at least one keratolytic agent (e.g., selected from salicylic acid, lactic acid and urea) may function as an exfoliant(s) which may act to remove mass of dead cells on the skin, including e.g., cells of the keratin layer, that may pile up for example above skin cancer or skin tumors that have not yet pushed up on the surface of the skin. This action may help the glycoalkaloids in the compositions of the present invention to access, interact and kill cancer or tumors cells on the skin without also killing normal uninfected or non-cancerous cells.

Methods of Preparation

Pharmaceutical compositions and medicaments of the present invention may include the glycoalkaloid(s) of the invention, together with the at least one viscosity modifier and at least one keratolytic agent e.g., as pharmaceutically acceptable carriers, excipients and/or diluents. Optionally the pharmaceutical compositions or medicaments of the present invention may further include one or more additional pharmaceutically acceptable carriers, excipients or diluents, as well as other agents commonly used in the preparation of pharmaceutically acceptable compositions.

Methods for the preparation of compositions or medicaments of the present invention comprising one or more active ingredients are generally known in the art. Such compositions will generally be formulated for the mode of delivery that is to be used and will usually include one or more pharmaceutically acceptable carriers, excipient and/or diluent.

In one example, a method of preparing the compositions or medicaments of the present invention comprises combining and/or admixing and/or dissolving one or more glycoalkaloids of formula I according to the present invention with a pharmaceutically acceptable carrier, diluent and/or excipient.

In another example, the method involves preparing compositions or medicaments comprising plurality of different glycoalkaloids, whereby the method comprises separately combining and/or admixing and/or dissolving each of the different glycoalkaloids with a pharmaceutically acceptable carrier, diluent and/or excipient so as to create a discrete dosage unit for separate administration of each different glycoalkaloid.

For example, the method of preparing the compositions or medicaments of the invention may comprise dissolving, combining and/or admixing the glycoalkaloid(s) with a pharmaceutically acceptable carrier, diluent and/or excipient suitable for topical delivery of the composition. In one such example, the carrier, diluent and/or excipient may be aqueous or non-aqueous. In another example, the pharmaceutically acceptable carrier, excipient and/or diluent will comprise any one or both of said at least one viscosity modifier and said at least one keratolytic agent of the present invention. Optionally, the method may further include dissolving and/or combining and/or admixing the glycoalkaloid and/or at least one viscosity modifier and/or at least one keratolytic agent with one or more additional pharmaceutically acceptable carriers, excipients or diluents, as well as other agents commonly used in the preparation of pharmaceutically acceptable compositions.

A "pharmaceutically acceptable carrier" or a "pharmaceutically acceptable excipient" or a "pharmaceutically acceptable diluent" is a material that is not biologically or otherwise undesirable, i.e., the material can be applied to an individual along with the active agents without causing unacceptable biological effects or interacting in a deleterious manner with any of the other components of the composition in which it is contained.

In one example, the compositions and medicaments of the invention include as carriers, excipients and/or diluents the one or more viscosity modifiers and the one or more keratolytic agents of the present invention as described herein above.

Alternatively, or in addition the compositions or medicaments of the invention may further comprise suitable carriers, excipient and diluents that are pharmaceutically acceptable and compatible with the active ingredient. Some examples of suitable carriers, excipient and diluents include, without limitation, water, saline, ethanol, dimethylsulfoxide (DMSO), dextrose, cyclodextrins such as hydroxy propyl beta-cyclodextrin, glycerol, teric and ecoteric fatty acid ethoxylates, lactose, sucrose sorbitol, mannitol, starches, gum acacia, calcium phosphates, alginate, tragacanth, gelatine, calcium silicate, microcrystalline cellulose, polyvinylpyrrolidone, cellulose, water syrup, methyl cellulose, methyl and propylhydroxybenzoates, talc, magnesium stearate and mineral oil or combinations thereof.

The compositions and medicaments of the present invention can additionally include lubricating agents, pH buffering agents, wetting agents, emulsifying and suspending agents or preserving agents. Examples of such suitable additional agents include:

a) surfactants and polymers including, but not limited to polyethylene glycol (PEG), polyvinylpyrrolidone (PVP), polyvinylalcohol, crospovidone, polyvinylpyrrolidone-polyvinylacrylate copolymer, cellulose derivatives, hydroxylpropylmethyl cellulose, hydroxylpropyl cellulose, carboxymethylethyl cellulose, hydroxylpropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate; and/or b) binding agents such as various celluloses and cross-linked polyvinylpyrrolidone, microcrystalline cellulose; and/or c) lubricating agents such as agents that act on the flowability of a powder to be compressed, including colloidal silicon dioxide, talc, stearic acid, magnesium stearate, calcium stearate, silica gel; and/or d) preservatives such as potassium sorbate, methylparaben, propylparaben, benzoic acid and its salts, other esters of parahydroxylbenzoic acid such as butylparaben, alcohols such as ethyl or benzyl alcohol, phenolic chemicals such as phenol, or quarternary compounds such as benzalkonium chloride; and/or e) buffers; and/or f) diluents such as pharmaceutically acceptable inert fillers, such as microcrystalline cellulose, lactose, dibasic calcium phosphate, saccharides, and/or mixtures of any of the foregoing; and/or g) wetting agents such as corn starch, potato starch, maize starch, and modified starches, croscarmellose sodium, crosspovidone, sodium starch glycolate, and mixtures thereof; and/or h) gelling (emulsion-stabilizing) agents such as: guar gum, locust bean gum, xanthan gum, gelatin, and cellulose derivatives (such as hydroxylethylcellulose).

The particular selection of constituent that can be included in the compositions or medicaments described herein will generally depend on the active agents and the ailment to be treated.

Compositions and medicaments of the invention are adapted for topical delivery. Any topical delivery systems may be appropriate for administering the compositions of the present invention depending upon the preferred treatment regimen.

Topical formulations as described above may be produced by dissolving or combining or admixing the active agent in an aqueous or non-aqueous carrier. In general, any liquid, cream, or gel, or similar substance that does not appreciably react with the active or any other of the ingredients that may be introduced into the composition and which is non-irritating is suitable. Appropriate non-sprayable viscous, semi-solid or solid forms can also be employed that include a carrier compatible with topical application and have a dynamic viscosity preferably greater than water.

Suitable formulations are well known to those skilled in the art and include, but are not limited to, solutions, suspensions, emulsions, creams, gels, ointments, powders, liniments, salves, aerosols, transdermal patches, etc, which are, if desired, sterilized or mixed with auxiliary agents, e.g., preservatives, stabilizers, emulsifiers, wetting agents, fragrances, colouring agents, odour controllers, thickeners such as natural gums etc. Particularly preferred topical formulations include ointments, creams or gels.

Ointments generally are prepared using either (1) an oleaginous base, i.e., one consisting of fixed oils or hydrocarbons, such as white petroleum or mineral oil, or (2) an absorbent base, i.e., one consisting of an anhydrous substance or substances which can absorb water, for example anhydrous lanolin. Customarily, following formation of the base, whether oleaginous or absorbent, the active agent is added to an amount affording the desired concentration.

Creams are oil/water emulsions. They consist of an oil phase (internal phase), comprising typically fixed oils, hydrocarbons and the like, waxes, petroleum, mineral oil and the like and an aqueous phase (continuous phase), comprising water and any water-soluble substances, such as added salts. The two phases are stabilised by use of an emulsifying agent, for example, a surface active agent, such as sodium lauryl sulfate; hydrophilic colloids, such as acacia colloidal clays, veegum and the like. Upon formation of the emulsion, the active agent is customarily added in an amount to achieve the desired concentration. In one example a stable cream formulation according to the present invention encompasses cream formulations comprising glycoalkaloid(s) wherein there substantially little or no separation of the oil and water phases of the cream after storage of the formulation at room temperature or at 25° C. after at least 3 months or at least 6 months or at least 12 months or at least 24 months or at least 36 months or at least 48 months after manufacture of the cream formulation.

Gels comprise a base selected from an oleaginous base, water, or an emulsion-suspension base. To the base is added a gelling agent that forms a matrix in the base, increasing its viscosity. Examples of gelling agents are hydroxypropyl cellulose, carbomers, acrylic acid polymers and the like. Customarily, the active is added to the formulation at the desired concentration at a point preceding addition of the gelling agent.

The customary amount of a topical formulation to be applied to an affected tissue will depend upon an affected tissue size and concentration of the active in the formulation.

Controlled release topical formulations may be desirable. The compositions could be incorporated into an inert matrix that permits release by either diffusion or leaching mechanisms i.e., gums. Slowly degenerating matrices may also be incorporated into the pharmaceutical composition. Another form of a controlled release is by a method based on the Oros therapeutic system (Alza Corp.), i.e. the composition is enclosed in a semipermeable membrane which allows water to enter and push the composition out through a single small opening due to osmotic effects. Some enteric coatings also have a delayed release effect.

A mix of materials might be used to provide the optimum film coating. Film coating may be carried out in a pan coater or in a fluidised bed or by compression coating.

The active agents may be included in the compositions as fine multiparticulates in the form of granules or pellets of particle size about 1 mm. The formulation for capsule administration could also be as a powder, lightly compressed plugs or even as tablets. The active agents may also be included in the compositions as fixed-dose inhalation powder capsules formulated to be applied to inhalers e.g., similar to those powder capsules utilised by the ULTIBRO® BREEZHALER®. The active agent(s) could be prepared by compression. Micro particles may be made by a variety of methods known to those in the art, for example, solvent evaporation, desolvation, complex coacervation, polymer/polymer incompatibility, interfacial polymerisation etc.

Hydrophilic polymers forming the microparticles may be attached to a targeting protein that acts to enable the micro particle to specifically bind selected target cells or tissues bearing the target molecule (e.g. characteristic marker). For example, the hydrophilic polymers may be conjugated to the Fab' fragment of an antibody. Smaller peptides from the hypervariable region or from another peptide interacting with a specific cell surface ligand may also be conjugated to the complexes. It is most preferred that the antibodies or antibody fragments are directed against target molecules associated with cancerous tissues or cells.

Therapeutic Uses

Therapeutic uses of the compositions and medicaments of the invention include treatment e.g., topical treatment of various diseases such as in the treatment of cancer, viral infections, bacterial infections, parasitic infections, fungal infections, inflammatory diseases and/or psoriasis.

In one embodiment, the compositions and medicaments of the present invention are for the treatment e.g., topical treatment of skin cancer and/or skin tumours.

Methods of Treatment

The compositions and medicaments of the invention may be applied clinically for the treatment of various diseases such as in the treatment of cancer, viral infections, bacterial infections, parasitic infections, fungal infections, inflammatory diseases and/or psoriasis. Thus the compositions and medicaments of the present invention may lead to the development of novel treatments for a variety of diseases.

Accordingly, the invention also provides a method of treating a patient having or suffering from a dermal disease associated with cancer, viral infections, bacterial infections, parasitic infections, fungal infections inflammatory diseases and/or psoriasis, said method comprising the step of applying to the disease state a therapeutically effective amount of a composition as described herein.

In a preferred form the present invention also provides a method for treating a tumorous growth comprising the step of administering a therapeutically effective synergistic amount of a composition described herein. In another preferred form the present invention also provides a method for treating a skin cancer and/or skin tumorous growth comprising the step of topically applying a therapeutically effective amount of a composition described herein to an area of the skin comprising said skin cancer and/or skin tumorous growth.

Whilst not being bound by any theory and proposed mechanism of action, applicant believes the compositions described herein are advantageous because they deliver a substantially stable formulation with reduced or minimal break down of the glycoalkaloid active agents. In this regard, it is hypothesised that the glycoalkaloid composition renders infected or target disease cells (e.g., cells of dermal disease state such as cancer cells, cells forming tumorous growth, cells infected with bacteria, virus, parasite or fungus, skin cells associated with psoriasis and/or inflammatory response on the skin) more accessible to the composition e.g. by increasing membrane, particularly the nuclear membrane, permeability.

In a particularly preferred form of the invention the composition is used to treat a tumorous ailment. In this instance the composition may also include a second component in the form of at least one chemotherapeutic agent with a nuclear mechanism of action.

Combination of glycoalkaloids and chemotherapeutic agents described herein exhibit interesting properties when contacted with cancerous cells ex vivo. When administered to patients, the composition provides better patient outcomes relative to the respective monotherapies and relative to the additive effects of the respective monotherapies. In this regard, the lower doses may avoid or ameliorate one or more side effects associated with the chemotherapeutic agents, when administered at the accepted dose used for monotherapy.

The tumorous growth may be associated with a range of cancers including cancer selected from the group consisting of: melanomas and non-melanoma skin including lignin melanoma, solar keratosis, keratoacanthoma, basal cell carcinoma, squamous cell carcinoma (e.g., cutaneous superficial squamous cell carcinoma) and actinic keratosis.

The compositions used in the method of the invention may also comprise a pharmaceutically acceptable carrier.

Where the composition comprises compounds other than the identified glycoalkaloids the other compounds may be administered in separate dosage forms. When administered separately, the compositions may be administered simultaneously or sequentially. For the purposes of the present invention "simultaneously" means that the compositions are administered at the same time or within one hour of each other. When the compositions are administered greater than one hour apart they are deemed to be administered sequentially.

Compositions of the present invention should be administered in dosage unit form that is therapeutically effective. Dosage unit form as used herein refers to physically discrete units suited as unitary dosages for the subjects to be treated, each unit containing a quantity of active material calculated to produce the desired therapeutic effect in association with the required pharmaceutical carrier. The specification for the dosage unit forms of the invention are dictated by and directly dependent on at least (a) the unique characteristics of the active material and the particular therapeutic effect to be achieved and (b) the limitations inherent in the art of compounding such an active material for the treatment sought. Thus, the quantity of active compound to be administered will be largely dependent on the toxicity and specific activity of compound, the subject to be treated and the degree of treatment required. Precise amounts of compound required to be administered may depend on the judgement of the practitioner and may be peculiar to each subject. Preferably, the dosages of the active agents administered according to the combination therapy of the present invention are less than the conventional dosages of the same active agents when used in monotherapy.

The compositions and medicaments of the present invention may be formulated for daily or periodic administration e.g., topical administration. For example, the compositions and medicaments may be administered daily for a period of at least about 3 days or at least 4 days or at least 5 days or at least 6 days, or at least 1 week or at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks or at least about 6 months or at least about one year or more than one year. In one preferred example, the composition is administered for a period of at least 3 days. In another preferred example, the composition is administered for at least about 13 weeks or at least about 3 months.

In another example, the composition may be administered periodically, such as, twice a day or three times a day or more than three times a day, or every second day or every third day or every fourth day or every fifth day or every sixth day or every second week for a period of at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks or at least about 6 months or at least about one year or more than one year.

In one preferred example, the composition is administered at least twice a day or at least every 12 hours for at least 3 consecutive days. In an alternative example, the composition may be administered up to 10 applications with at least 0.5 hour spans daily to achieve therapeutic effect (e.g., to remove the cancer or tumour skin lesion) more rapidly.

In another example, the composition may be administered for an administration period of at least about 1 week or at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks or at least about 6 months or at least about one year or more than one year, followed by a period of discontinuance, followed by an administration period of at least about 1 week or at least about 2 weeks or at least about 3 weeks or at least about 4 weeks or at least about 5 weeks or at least about 6 weeks or at least about 7 weeks or at least about 8 weeks or at least about 9 weeks or at least about 10 weeks or at least about 11 weeks or at least about 12 weeks or at least about 13 weeks or at least about 14 weeks or at least about 15 weeks or at least about 16 weeks or at least about 17 weeks or at least about 18 weeks or at least about 19 weeks or at least about 20 weeks or at least about 21 weeks or at least about 22 weeks or at least about 23 weeks or at least about 24 weeks or at least about 25 weeks or at least about 6 months or at least about one year or more than one year.

In one example, the composition or medicament of the present invention comprises about 0.005% (w/w) glycoalkaloids. In another example, the composition or medicament of the present invention may be applied topically to an affected area of the skin at least twice daily for at least 3 consecutive days e.g., with an occlusive dressing such as twice daily or every 12 hours for 3 consecutive days.

Although more frequent applications may also be possible e.g., every 0.5 hour up to 10 consecutive applications.

Preferably, (e.g., if the composition or medicament is a cream or gel formulation) the composition or medicament is applied thinly and evenly over the skin treatment area, such that the lesion or dermal disease state is covered with the occlusive dressing to avoid drying out the medicament or composition once applied to the skin. Preferably, the medicament or composition is not applied in large quantity so as to extend the application of the composition or medicament more than 0.5 cm onto the apparently normal skin surrounding the edge of the lesion or affected area of the skin.

In one example, the composition or medicament of the present invention is applied until the cancer/tumour lesion is cleared and/or the bacterial, viral, fungus infection and/or inflammation and/or psoriasis is cleared, and preferably the skin lesion/diseased condition on the skin is replaced with normal healthy skin (e.g., as determined visually).

EXAMPLES

Example 1: Preparation of Sugar Free Solasodine Glycoside

This example demonstrates a method for making a preparation of a glycoalkaloid which is essentially devoid (i.e., without) free saccharides including of the type which inhibit an interaction between the glycoalkaloids and their target cell.

A sugar free solasodine glycoside preparation was prepared according to the following: 50 kg *Solanum Sodomaeum* berries were put through a commercial meat mincer (fitted with I.HP electric motor 1425 rpm) with a sieve size of 3 mm.

The slurry was diluted with 3% acetic acid (pH 2.5) (food grade) to a volume of 200 L. This semi-solid solution was treated with a Silverson homogenizer for 15 minutes. Mixing was continued for another 4 hours using a SS rod with arms mixer at room temperature at 30 rpm (Flamingo CMG 0.75 kw variable speed control meter).

The solution was allowed to stand overnight without mixing. The solution was subsequently filtered through a muslin cloth. The filtrate was then subjected to a flow through centrifuge (3.5HP) at 1455 rpm. The clear filtrate was heated to 50° C. in a stainless steel double jacketed bowl. Concentrated ammonia (L R Grade) was added until approximately pH 10. A precipitate was observed. The precipitate was allowed to settle and cool (approx. 24 hrs). The supernatant was carefully decanted. The precipitate was dissolved in 25 L of 3% aqueous acetic acid. The solution was centrifuged through flow through centrifuge as above. The supernatant was collected in an SS double jacketed bowl and heated to 50° C. with continuous stirring (30 rpm, 30 min).

The glycoalkaloids were re-precipitated by the addition of concentrated ammonia solution until approximately pH 10. The solution was allowed to cool and the precipitate was allowed to settle (approx. 24 hrs). The supernatant was carefully decanted and the precipitate was washed with 50 L water and allowed to settle for 24 hrs as before. The supernatant was decanted. This procedure was repeated four times.

The precipitate was finally dissolved in 10 L alcohol at 75° C. and filtered whilst hot through Whatman No. 1 filter paper. The supernatant was dried at 50° C. This yielded a fine, semicrystalline powder. The yield was 505 g which was 1.01%.

Any aglycone solasodines were removed by washing the extract in chloroform. The solasodine was soluble in the chloroform phase and the sugars were soluble in the aqueous phase. The glycoalkaloids remained insoluble under all these conditions.

Example 2: Stability Analysis of Solasodine Glycosides

In the present study, cream formulations were prepared from the sugar free solasodine glycoside semi crystalline preparation e.g., as prepared according to the method in Example 1. The actual cream formulations were made as detailed in WO 2000061153 A1 (which is incorporated herein by reference in its entirety). Emulsifying wax, white soft paraffin (10% w/w), liquid paraffin (10% w/w), propylene glycol (5%) and water were used to provide a cream base, and chlorocresol (0.1%) was included as a preservative.

In the case of previous human skin cancer studies, cream formulations comprising glycoalkaloids were tested within five months after the manufacturing of the cream. The results were remarkable. With these studies only the presence of the active glycoalkaloids were shown. However, their concentrations were not shown. See for example WO 2000061153A1.

In the present study, cream formulations were prepared from the sugar free solasodine glycoside semi crystalline preparation e.g., as prepared according to the method in Example 1. The actual cream formulations were made as detailed in WO 2000061153 A1 (which is incorporated herein by reference in its entirety). Emulsifying wax, white soft paraffin (10% w/w), liquid paraffin (10% w/w), propylene glycol (5%) and water were used to provide a cream base, and chlorocresol (1%) was included as a preservative.

Stability of the solasodine glycoside in a cream formulation containing by weight 5% urea and 10% salicylic acid but no lactic acid and no emulsion-stabilising agent was tested over a period of 48 months from the time of preparation of the formulation, with the results shown in Table 1. Visual appearance was conducted by comparison to standard commercially available solamargine cream composition. High-Performance Liquid Chromatography (HPLC) to determine quantity of solamargine in the cream, substantially as described in WO 2000061153 A1.

Here we report that, even after removing free (unconjugated) sugars by washing semi crystalline solasodine rhamnosides (e.g., as outlined in Example 1) prior to inclusion of the solasodine rhamnosides in the composition and using the composition in a cream formulation to treat skin cancers, instability of the solasodine rhamnosides persists.

TABLE 1

Stability data for solamargine in cream formulation containing by weight 5% urea, 10% salicylic, no lactic acid, and no emulsion-stabilising agent.

| | Storage Temp. 25°C, 60% Relative Humidity - Months | | | | | | | | | |
|---|---|---|---|---|---|---|---|---|---|---|
| Test | 0 | 3 | 6 | 9 | 12 | 18 | 24 | 36 | 42 | 48 |
| Identification | | | | | | | | | | |
| Appearance | C | C | F | F | F | F | F | F | F | F |

TABLE 1-continued

Stability data for solamargine in cream
formulation containing by weight
5% urea, 10% salicylic, no lactic acid,
and no emulsion-stabilising agent.

Storage Temp. 25°C, 60% Relative Humidity - Months

| Test | 0 | 3 | 6 | 9 | 12 | 18 | 24 | 36 | 42 | 48 |
|---|---|---|---|---|---|---|---|---|---|---|
| HPLC Assay | | | | | | | | | | |
| Solamargine µg/g cream | 18.3 | 19 | 21.1 | 9.2 | 7.3 | 6.8 | 5.1 | 5.3 | 5.1 | 5.2 |

C = Comply
F = Fail

Furthermore, when this cream formulation was used in the clinical setting over extended periods, it was observed that with ageing of the cream formulation, it appeared that the efficacy of the cream formulation decreased with time.

Concurrently, it was noticed that the cream's stability was very temperature dependent, resulting in the separation of the oil and water phases at room temperatures.

Further studies determined that there were two identifiable flaws in the cream formulation:
Heat instability of the cream formulation even at room temperature; and
Degradation of the glycoalkaloids in the cream formulation.

These two flaws were further explored to determine whether they could be overcome.

In order to inhibit the degradation of the solasodine rhamnosides, lactic acid at varying concentrations ranging from 1 to 10% (w/w) was added to the cream formulations. One immediate problem arose. The emulsion of the cream was destabilised at concentrations of lactic acid above 4% (w/w).

In order to overcome the above-documented lack of stability of the cream formulation, the original formulated cream had to be modified.

Various emulsion-stabilising agents were investigated. Ultimately Xanthan gum was selected for the purpose of emulsion stability. BEC cream formulations were studied using varying amounts of Xanthan gum (Xg). 0.2% (w/w) of Xg in the formulation resulted in slight thickening. The optimum concentration in the cream was 1.0% of Xg. A thick heat stable emulsion was obtained. Larger Xg resulted in undesirable slimy textures of the cream.

Based on these achievements it was then possible to study increasing concentrations of lactic acid and/or other components in the cream formulations and determine how these concentrations relate to the stability and prevention of degradation by hydrolysis of the solasodine rhamnosides in the creams.

It was determined that lactic acid at concentrations of above 4% by weight in the cream formulation was optimum for the stability of the cream.

This was surprising since it was anticipated that lactic acid at these concentrations as well as 10% (w/w) salicylic acid (present in the creams as keratolytic agents) would result in a very low pH with high acidity and would therefore cause hydrolysis of the BEC glycoalkaloids. This was shown not to be the case.

HCl at low concentrations (less than 1% by weight) are known to hydrolyse glycoalkaloids. HCl is a strong acid and has a pka value of less than −2. Lactic acid is a weak acid and has a pka value of 3.86. A weak acid has a pka value in the approximate range of −2 to 12 in water. Strong acids have a pka value of less than −2. Salicylic acid, although not very soluble in water, is soluble in the cream emulsion and has a pka value of 2.97. Hence the difference in acidity of HCl when compared with lactic acid and salicylic acid is in the vicinity of 5 orders of magnitude. This may explain why the BEC glycoalkaloids are substantially stable in the cream form in the presence of weak acids at the concentrations of up to 10% lactic acid and up to 10% salicylic acid by weight.

To mimic the characteristics of cell suspension media, where very low concentrations of these glycoalkaloids had efficacious anticancer properties, particular excipients were added to the glycoalkaloid-containing cream formulation as shown in Table 2, to create a new and more stable formulation than that originally prepared or described above.

TABLE 2

Substantially stable formulation

| Excipient | Range (w/w) | Preferred Amount (w/w) |
|---|---|---|
| Xanthan gum | 0.2-2% | 1% |
| Lactic acid | 4-10% | 10% |
| salicylic acid | 5-10% | 10% |
| Urea | 3-5% | 5% |

In particular, the effects of addition of salicylic acid, urea and xanthan gum on the stability of the resulting formulation were investigated as shown in Table 3.

TABLE 3

Stability data for solamargine in cream formulation containing by weight
5% urea, 10% salicylic, 10% lactic acid, and 1% Xanthan gum.

Storage Temp. 25° C., 60% Relative Humidity - Months

| Test | 0 | 3 | 6 | 9 | 12 | 18 | 24 | 36 | 42 | 48 |
|---|---|---|---|---|---|---|---|---|---|---|
| Identification | | | | | | | | | | |
| Appearance | C | C | C | C | C | C | C | C | C | C |
| HPLC Assay | | | | | | | | | | |
| Solamargine µg/g cream | 20.6 | 23.1 | 19.8 | 21.2 | 23.1 | 20.4 | 22.1 | 19.8 | 19.6 | 21.2 |

C = Comply
F = Fail

Indeed, the presence of salicylic acid (10% w/w), urea (5% w/w) and Xanthan gum (1% w/w) in a topical cream formulation was advantageous in obtaining remarkable treatment results of skin cancers using very low concentrations of BEC, approximating the level of BEC, shown to be highly efficacious in cancer cell culture studies.

As aforementioned, the stability and complete efficacy of the original glycoalkaloid emulsion cream formulation containing 5% urea, 10% salicylic acid, no lactic acid, and no emulsion-stabilising agent for the treatment of skin cancers had abundant limitations that restricted its therapeutic use.

Based on the studies with Xanthan gum and lactic acid, a particular exemplary formulation, shown in Table 2, was devised containing specific excipients to overcome the flaws of the original emulsion instability and BEC glycoalkaloids instability in cream formulations.

This novel topical cream formulation with appropriate excipients has resulted in a substantially stable, efficacious novel topical cream formulation with a shelf life of over 4 years when used clinically.

Example 3: Effects of Free (Unconjugated) Sugars on the Therapeutic Activity of Glycoalkaloids This example demonstrates that free (unconjugated) sugar moieties such as free rhamnose decreases therapeutic anti-cancer/tumour efficacy of SR glycoalkaloids of the present invention.

To determine the effect of free sugar moieties on the anti-cancer activity of SR glycoalkaloids of the present invention, anti-cancer activity of increasing concentrations of BEC glycoalkaloids extract was determined under cell culture conditions in the presence of no free rhamnose and separately, in the presence of 5 mM rhamnose. To this effect, melanoma cancer cells were incubated with increasing concentrations (0-20 µg/mL) of BEC extract (which consisted of a constant mixture of solamargine, solasonine and di- and mono-glycosides of solasodine) in the presence or absence of free rhamnose. The results are shown in FIG. 1.

As shown in FIG. 1, increasing concentrations of BEC results in decreasing melanoma cell survival, with an $LD_{50}$ of 12 µg/mL of BEC and $LD_{100}$ of approximately 20 µg/mL of BEC. When 5 mM of free rhamnose was co-administered with the BEC to melanoma cancer cells, virtually all the melanoma cells survive.

Accordingly, this example demonstrates that free sugars such as rhamnose exert a protective effect against anti-cancer and/or anti-tumour therapeutic efficacy of glycoalkaloids compounds of the present invention.

These data complement the in vivo studies with Sarcoma 180 mice described in W2000061153A1.

Example 4: Effects of Various Drug Combinations on Tumour Cells Ex-Vivo

This example demonstrates synergistic anti-cancer effect of compositions comprising a glycoalkaloid of the present invention when tested in combination with other chemotherapeutic agents e.g., agents having a nuclear mechanism of action, as determined by ex-vivo assays measuring cell death (by apoptosis) of cancer or tumour cells.

Data supports the proposition that laboratory results from EVA (ex vivo analysis) correlate very well with clinical observations. This approach has been supported by several peer reviewed articles comprising over 650 published clinical correlations (see, for example, Principles and Practice of Oncology Updates: Vol. 7, No. 12, 1993) which are summarized in Table 4. As shown in Table 4, these published clinical correlations indicate that EVA has a sensitivity of 96.1% and a specificity of 87.1% (Table 4). Further, the EVA chemo-sensitivity assay has been shown to correlate with response, time to progression and survival. Tumour specific positive and negative predictive accuracy is provided in more detail in Table 4 below:

TABLE 4

Predictive accuracy of cell death assays in selected solid tumour types.

| Type | Number* | Predictive Positive Accuracy | Predictive Negative Accuracy | False Positive | False Negative |
|---|---|---|---|---|---|
| Breast | 194 | 82.9% | 88.9% | 6.4% | 0.0% |
| Colon | 54 | 80% | 97.7% | 3.7% | 1.9% |
| NSCLC | 47 | 66.7% | 93.1% | 12.8% | 4.3% |
| GYN | 345 | 77% | 87.9% | 14.2% | 4.6% |
| SCLC | 19 | 50% | 84.6% | 15.8% | 10.5% |
| Total | 659 | 78.4% | 90.1% | 12.9% | 3.9% |
| Sensitivity | | | | | 96.1% |
| Specificity | | | | 87.1% | |

Predictive Positive Accuracy: when the assay predicted sensitivity and there was a response
Predictive Negative Accuracy: when the assay predicted resistance and there was no response.
*Number of published clinical correlations It was once thought that cancer cells outgrow normal healthy cells. It is now known that cancer cells actually outlive normal cells; it is not that they grow too much, they in fact live too long. Ex vivo analyses take this into account, and measure the process of cell death rather than cell proliferation/growth. The principal ex vivo assay technique measures apoptotic endpoints which are more reflective of the effects of chemotherapy in vivo. The ex vivo assay can also measure non-apoptotic endpoints including: ATP content (luminescent), MTT (mitochondrial activity) and membrane integrity methodologies, as additional cell death endpoints. As Coramsine® has previously displayed a non-apoptotic mode of action, ex vivo studies testing Coramsine® were carried out using non-apoptotic endpoints.

Fresh samples of human tumours were disaggregated mechanically and enzymatically and spheroids were resuspended in modified RPMA 1640 generally in accordance with the methods set forth in Nagourney R. A. et al (2003).

The resuspended spheroids were treated with CORAMSINE® [which is composed of the two solasodine glycoalkaloids, solasonine and solamargine at a ratio of 1:1 (w/w)] in combination with various other chemotherapeutic agents generally in accordance with the methods set forth in Nagourney R. A. et al (2003). In some instances, CORAMSINE® was tested in combination with multiple other chemotherapeutic agents.

Synergy was determined using the median effect technique of Chou and Talalay (1987) and generally in accordance with the methods set forth in Nagourney R. A. et al (2003).

Results are set out in the Tables hereunder. The "activity" information is related as Index Concentration 50% cell survival. Relevant abbreviations/equivalent nomenclatures are: 5FU=5-Fluorouracil; BCNU=Carmustine (BiCNU®); CAMP=a combination of cyclophosphamide (Cytoxan®), doxorubicin (Adriamycin®), methotrexate (Mexate®) and procarbazine (Matulane®); CDDP=Cisplatin; DOX=Doxorubicin (Adriamycin®, hydroxyldaunorubicin); DTIC (®)=Dacarbazine (DIC, imidazole carboxamide);

GEM=Gemcitabine (Gemzar®); IRES=Iressa® (gefitinib); L-OHP=oxaliplatin (Eloxatin®); MMC=mitomycin C; NAV=Navelbine® (vinorelbine); NM=Nitrogen Mustard (mechlorethamine, chlormethine, mustine, Mustargen®); TAX=Taxol® (paclitaxel); TMTX=Trimetrexate; TMZ=Temozolomide (Temodar®, Temodal®); TOPO=Topotecan (Hycamtin) and COR=Coramsine®.

1. Renal

SYNERGY RENAL COUNT

| DRUGS | SYNERGY | PART | MIXED | NO SYN | ANTAG |
|---|---|---|---|---|---|
| 5FU + CDDP | 1 | 1 | 5 | 5 | 9 |
| 5FU + CDDP + GEM | 1 | 2 | 3 | 0 | 5 |
| 5FU + INF | N/A | N/A | N/A | N/A | N/A |
| COR + 5FU + CDDP | 0 | 1 | 1 | 1 | 11 |
| COR + 5FU + CDDP + GEM | 0 | 1 | 4 | 1 | 6 |
| COR + 5FU + INF | N/A | N/A | N/A | N/A | N/A |
| COR + CDDP + GEM | 0 | 1 | 1 | 0 | 12 |
| COR + DOX | 4 | 0 | 2 | 3 | 11 |
| COR + GEM | 0 | 4 | 5 | 4 | 8 |
| COR + INF | N/A | N/A | N/A | N/A | N/A |
| COR + NM | 2 | 0 | 1 | 4 | 14 |
| COR + TOPO | 3 | 0 | 6 | 0 | 12 |
| CDDP + GEM | 5 | 3 | 8 | 1 | 5 |

RENAL PERCENT SYNERGY

| DRUG | % SYNERGY | % PART | % MIXED | % NO SYN | % ANTAG | TOTAL COUNT |
|---|---|---|---|---|---|---|
| 5FU + CDDP | 5% | 5% | 24% | 24% | 43% | 21 |
| 5FU + CDDP + GEM | 9% | 18% | 27% | 0% | 45% | 11 |
| 5FU + INF | N/A | N/A | N/A | N/A | N/A | N/A |
| COR + 5FU + CDDP | 0% | 7% | 7% | 7% | 79% | 14 |
| COR + 5FU + CDDP + GEM | 0% | 8% | 33% | 8% | 50% | 12 |
| COR + 5FU + INF | N/A | N/A | N/A | N/A | N/A | N/A |
| COR + CDDP + GEM | 0% | 7% | 7% | 0% | 86% | 14 |
| COR + DOX | 20% | 0% | 10% | 15% | 55% | 20 |
| COR + GEM | 0% | 19% | 24% | 19% | 38% | 21 |
| COR + INF | N/A | N/A | N/A | N/A | N/A | N/A |
| CORE + NM | 10% | 0% | 5% | 19% | 67% | 21 |
| COR + TOPO | 14% | 0% | 29% | 0% | 57% | 21 |
| CDDP + GEM | 23% | 14% | 36% | 5% | 23% | 22 |

ACTIVITY RENAL

| DRUGS | COUNT | AVG IC50 | STD·D |
|---|---|---|---|
| 5FU + CDDP | 21 | 44.86 | 11.22 |
| 5FU + CDDP + GEM | 12 | 77.58 | 36.27 |
| 5FU + INF | 19 (5) | 4474.00 | 1232.33 |
| COR + 5FU + CDDP | 14 | 25.71 | 14.66 |
| COR + 5FU + CDDP + GEM | 12 | 50.67 | 28.32 |
| COR + 5FU + INF | 13 | 1347.23 | 567.91 |
| COR + CDDP + GEM | 14 | 45.00 | 27.78 |
| COR + DOX | 20 | 8.13 | 2.84 |
| COR + GEM | 21 | 42.24 | 15.60 |
| COR + INF | 18 (7) | 1211.00 | 441.98 |
| COR + NM | 21 | 8.18 | 2.43 |
| COR + TOPO | 21 | 8.03 | 2.50 |
| CDDP + GEM | 22 | 77.23 | 42.08 |

2. Colorectal

SYNERGY COLON COUNT

| DRUG | SYNERGY | PART | MIX | NO SYN | ANTAG |
|---|---|---|---|---|---|
| 5FU + CAMP | 4 | 5 | 3 | 2 | 5 |
| 5FU + L-OHP | 5 | 3 | 4 | 4 | 3 |
| COR + 5FU | 7 | 1 | 7 | 2 | 2 |
| COR + 5FU + L-OHP | 4 | 2 | 1 | 0 | 5 |
| COR + CAMP | 7 | 0 | 3 | 1 | 7 |
| COR + CAMP + 5FU | 3 | 0 | 3 | 0 | 4 |
| COR + L-OHP | 5 | 0 | 4 | 2 | 6 |
| COR + MMC | 9 | 0 | 3 | 3 | 5 |
| COR + TAX | 5 | 0 | 4 | 2 | 6 |
| COR + TMTX | 5 | 3 | 2 | 3 | 6 |
| COR + TOPO | 8 | 0 | 2 | 0 | 7 |

COLON PERCENT SYNERGY

| DRUG | % SYNERGY | % PART | % MIX | % NO SYN | % ANTAG | COUNT SYN |
|---|---|---|---|---|---|---|
| 5FU + CAMP | 21% | 26% | 16% | 11% | 26% | 19 |
| 5FU + L-OHP | 26% | 16% | 21% | 21% | 16% | 19 |
| COR + 5FU | 37% | 5% | 37% | 11% | 11% | 19 |
| COR + 5FU + L-OHP | 33% | 17% | 8% | 0% | 42% | 12 |
| COR + CAMP | 39% | 0% | 17% | 6% | 39% | 18 |
| COR + CAMP + 5FU | 30% | 0% | 30% | 0% | 40% | 10 |
| COR + L-OHP | 29% | 0% | 24% | 12% | 35% | 17 |
| COR + MMC | 45% | 0% | 15% | 15% | 25% | 20 |
| COR + TAX | 29% | 0% | 24% | 12% | 35% | 17 |
| COR + TMTX | 26% | 16% | 11% | 16% | 32% | 19 |
| COR + TOPO | 47% | 0% | 12% | 0% | 41% | 17 |

ACTIVITY COLON

| DRUG | COUNT | AVG IC50 | STD·D |
|---|---|---|---|
| 5FU + CAMP | 20 | 38.24 | 29.62 |
| 5FU + L-OHP | 20 | 25.93 | 17.68 |
| COR + 5FU | 21 | 12.36 | 6.21 |
| COR + 5FU + L-OHP | 12 | 10.47 | 6.43 |
| COR + CAMP | 19 | 15.46 | 10.80 |
| COR + CAMP + 5FU | 11 | 18.78 | 12.27 |
| COR + L-OHP | 18 | 5.44 | 2.38 |
| COR + MMC | 20 | 5.62 | 4.13 |
| COR + TAX | 17 | 10.82 | 7.37 |
| COR + TMTX | 19 | 11.66 | 8.53 |
| COR + TOPO | 18 | 6.22 | 4.94 |

3. Non-Small Cell Lung4 Cancer

SYNERGY NSCLC COUNT

| DRUGS | SYNERGY | PART | MIX | NO SYN | ANTAG |
|---|---|---|---|---|---|
| COR + CDDP | 5 | 2 | 6 | 0 | 8 |
| COR + CDDP + GEM | 2 | 0 | 1 | 1 | 7 |
| COR + CDDP + NAV | 7 | 1 | 2 | 0 | 1 |
| COR + CDDP + TAX | 0 | 1 | 4 | 1 | 6 |
| COR + CDDP + TOPO | 7 | 2 | 0 | 0 | 1 |
| COR + GEM | 8 | 4 | 6 | 0 | 2 |
| COR + IRES | 3 | 1 | 4 | 1 | 9 |
| COR + NAV | 1 | 8 | 6 | 1 | 4 |
| COR + TAX | 1 | 0 | 1 | 3 | 16 |
| COR + TMTX | 1 | 0 | 4 | 3 | 8 |
| COR + TOPO | 3 | 1 | 6 | 1 | 7 |
| CDDP + GEM | 12 | 2 | 3 | 1 | 1 |
| CDDP + NAV | 4 | 3 | 8 | 2 | 3 |
| CDDP + TAX | 4 | 1 | 4 | 2 | 9 |
| CDDP + TOPO | 3 | 2 | 4 | 2 | 3 |

NSCLC PERCENT SYNERGY

| DRUGS | % SYNERGY | % PART | % MIX | % NO SYN | % ANTAG | TOTAL COUNT |
|---|---|---|---|---|---|---|
| COR + CDDP | 24% | 10% | 29% | 0% | 38% | 21 |
| COR + CDDP + GEM | 18% | 0% | 9% | 9% | 64% | 11 |
| COR + CDDP + NAV | 64% | 9% | 18% | 0% | 9% | 11 |
| COR + CDDP + TAX | 0% | 8% | 33% | 8% | 50% | 12 |
| COR + CDDP + TOPO | 70% | 20% | 0% | 0% | 10% | 10 |
| COR + GEM | 40% | 20% | 30% | 0% | 10% | 20 |
| COR + IRES | 17% | 6% | 22% | 6% | 50% | 18 |
| COR + NAV | 5% | 40% | 30% | 5% | 20% | 20 |
| COR + TAX | 5% | 0% | 5% | 14% | 76% | 21 |
| COR + TMTX | 6% | 0% | 25% | 19% | 50% | 16 |
| COR + TOPO | 17% | 6% | 33% | 6% | 39% | 18 |
| CDDP + GEM | 63% | 11% | 16% | 5% | 5% | 19 |
| CDDP + NAV | 20% | 15% | 40% | 10% | 15% | 20 |
| CDDP + TAX | 20% | 5% | 20% | 10% | 45% | 20 |
| CDDP + TOPO | 21% | 14% | 29% | 14% | 21% | 14 |

ACTIVITY NSCLC

| DRUGS | COUNT | IC50 AVG | STD•D |
|---|---|---|---|
| COR + CDDP | 22 | 6.70 | 3.12 |
| COR + CDDP + GEM | 12 | 19.89 | 9.00 |
| COR + CDDP + NAV | 12 | 4.29 | 2.45 |
| COR + CDDP + TAX | 13 | 9.73 | 4.22 |
| COR + CDDP + TOPO | 12 | 4.33 | 1.99 |
| COR + GEM | 21 | 29.76 | 15.20 |
| COR + IRES | 19 | 9.15 | 6.23 |
| COR + NAV | 21 | 5.38 | 3.04 |
| COR + TAX | 22 | 12.26 | 4.65 |
| COR + TMTX | 18 | 16.75 | 8.73 |
| COR + TOPO | 20 | 6.17 | 2.77 |
| CDDP + GEM | 19 | 29.51 | 26.79 |
| CDDP + NAV | 20 | 2.72 | 2.48 |
| CDDP + TAX | 20 | 8.63 | 4.82 |
| CDDP + TOPO | 16 | 1.29 | 0.71 |

4. Melanoma

SYNERGY MELANOMA COUNT

| DRUGS | SYNERGY | PART | MIX | NO SYN | ANTAG |
|---|---|---|---|---|---|
| COR + BCNU | 2 | 0 | 1 | 0 | 5 |
| COR + CDDP | 3 | 1 | 2 | 0 | 6 |
| COR + CDDP + GEM | 0 | 1 | 0 | 0 | 8 |
| COR + CDDP + TAX | 0 | 0 | 0 | 2 | 6 |
| COR + DTIC | 4 | 1 | 1 | 1 | 5 |
| COR + NAV | 3 | 0 | 3 | 0 | 3 |
| COR + NM | 3 | 2 | 2 | 1 | 4 |
| COR + TAX | 1 | 0 | 2 | 3 | 6 |
| COR + TMZ | 2 | 0 | 1 | 1 | 5 |
| CDDP + GEM | 5 | 0 | 1 | 0 | 0 |
| CDDP + TAX | 3 | 0 | 1 | 1 | 5 |

MELANOMA % SYNERGY

| DRUGS | % SYNERGY | % PART | % MIX | % NO SYN | % ANTAG | TOTAL N |
|---|---|---|---|---|---|---|
| COR + BCNU | 25% | 0% | 13% | 0% | 63% | 8 |
| COR + CDDP | 25% | 8% | 17% | 0% | 50% | 12 |
| COR + CDDP + GEM | 0% | 11% | 0% | 0% | 89% | 9 |
| COR + CDDP + TAX | 0% | 0% | 0% | 25% | 75% | 8 |
| COR + DTIC | 33% | 8% | 8% | 8% | 42% | 12 |
| COR + NAV | 33% | 0% | 33% | 0% | 33% | 9 |
| COR + NM | 25% | 17% | 17% | 8% | 33% | 12 |
| COR + TAX | 8% | 0% | 17% | 25% | 50% | 12 |
| COR + TMZ | 22% | 0% | 11% | 11% | 56% | 9 |
| CDDP + GEM | 83% | 0% | 17% | 0% | 0% | 6 |
| CDDP + TAX | 30% | 0% | 10% | 10% | 50% | 10 |

ACTIVITY MELANOMA

| DRUGS | COUNT | AVG IC50 | STD•D |
|---|---|---|---|
| COR + BCNU | 8 | 7.68 | 3.55 |
| COR + CDDP | 12 | 5.49 | 3.50 |
| COR + CDDP + GEM | 10 | 27.68 | 29.15 |
| COR + CDDP + TAX | 10 | 10.97 | 3.82 |
| COR + DTIC | 12 | 69.42 | 68.36 |
| COR + NAV | 10 | 7.09 | 6.33 |
| COR + NM | 12 | 6.60 | 4.57 |
| COR + TAX | 12 | 10.45 | 5.03 |
| COR + TMZ | 9 | 62.67 | 44.08 |
| CDDP + GEM | 12 | 23.12 | 10.37 |
| CDDP + TAX | 10 | 6.42 | 3.76 |

As can be seen from the preceding tables, CORAMSINE acts synergistically with a range of chemotherapeutic agents with a nuclear mechanism of action, in respect of a range of representative cancers.

REFERENCES

Nagourney R. A., Sommers B. L., Harper S. M., Radecki S., Evans S. S. (2003) Ex vivo analysis of topotecan: advancing the application of laboratory-based clinical therapeutics. British Journal of Cancer 89, 1789-1795.

Chou T-C., Talalay P. (1987) Applications for the median-effect principle for the assessment of low-dose risk of carcinogens and for the quantitation of synergism and antagonism of chemotherapeutic agents. In New Avenues in Developmental Cancer Chemotherapy. Harrap K. R., Conneros T. A. (eds) pp 37-64, Orlando, FL: Academic Press Inc.

We claim:

1. A topical pharmaceutical composition comprising at least one glycoalkaloid, at least one viscosity modifier, at least one keratolytic agent, salicylic acid, and urea, wherein the at least one glycoalkaloid comprises at least one solasodine glycoside, wherein the at least one viscosity modifier is xanthan gum, and wherein the at least one keratolytic agent is lactic acid, and wherein
   the concentration of the xanthan gum is 0.2-2% by w/w,
   the concentration of the lactic acid is 5-10% by w/w,
   the concentration of the salicylic acid is 5-10% by w/w,
   the concentration of the urea is 3-5% by w/w, and
wherein the composition comprises
   15% by w/w cetomacrogol emulsifying wax,
   10% by w/w white soft paraffin,
   10% w/w liquid paraffin,
   5% by w/w propylene glycol,
   0.1% by w/w chlorocresol, and
   water,
and wherein the composition is an emulsion.

2. The composition according to claim 1, wherein the composition further comprises at least one chemotherapeutic agent with a nuclear mechanism of action.

3. The composition according to claim 1, wherein the composition includes by w/w xanthan gum 1%, lactic acid 10%, salicylic acid 10% and urea 5%.

4. The composition according to claim 1, wherein the composition is a cream.

5. The composition according to claim 1, wherein the composition is essentially without free rhamnose saccharides.

6. The composition according to claim 1, further comprising at least one keratolytic agent selected from: 3-hydroxypropionic acid, beta-hydroxybutyric acid, beta-hydroxy beta-methylbutyrate, carnitine, azelaic acid, benzoyl peroxide, trichloroacetic acid (TCA), carbolic acid (Phenol), croton oil, acetone, and sulphur.

7. The composition according to claim 1, comprising (i) a mixture of the triglycoside solasonine, the triglycoside solamargine, and mono- and di-glycosides of solasodine, or (ii) a mixture of the triglycoside solasonine and the triglycoside solamargine at a 1:1 ratio (w/w), and without mono- and di-glycosides of solasodine.

8. The composition according to claim 7, wherein the mixture in (i) is a mixture of glycoalkaloids consisting of 33% (w/w) being the triglycoside solasonine, 33% (w/w) being the triglycoside solamargine, and 34% (w/w) being mono- and di-glycosides of solasodine.

9. The composition according to claim 1, comprising at least one of the glycoalkaloids solasonine and solamargine.

10. The composition according to claim 1, wherein the composition is stable at room temperature or 25° C. and at 60% relative humidity.

11. The composition according to claim 10, wherein the composition is stable at room temperature or 25C and at 60% relative humidity such that at least 70% of the glycoalkaloids in the composition remain unhydrolysed or nondegraded after at least 6 months of storage of the composition at the room temperature or 25° C. and at 60% relative humidity.

12. The composition according to claim 10, having a shelf life of at least 4 years at room temperature or 25° C.

13. The composition according to claim 1, wherein the concentration of the at least one glycoalkaloid comprising the at least one solasodine glycoside in said composition is 0.001-10% by w/w.

14. The composition according to claim 13, wherein the concentration of the at least one glycoalkaloid comprising the at least one solasodine glycoside is said composition is 0.005% by w/w.

15. The composition according to claim 1, comprising a mixture of glycoalkaloids consisting of 33% (w/w) being the triglycoside solasonine, 33% (w/w) being the triglycoside solamargine, and 34% (w/w) being mono- and di-glycosides of solasodine, and wherein said mixture is present in said at a concentration of 0.005% (w/w).

16. A method of preparing the topical pharmaceutical composition according to claim 1, said method comprising at least one of combining and admixing a therapeutically effective amount of the at least one glycoalkaloid, an amount of the at least one viscosity modifier which is xanthan gum at the concentration of 0.2-2% (w/w), and an amount of the at least one keratolytic agent which is lactic acid at the concentration of 5-10% (w/w), and the salicylic acid at the concentration of 5-10% (w/w), and the urea at the concentration of the urea which is 3-5% by w/w, and 15% by w/w cetomacrogol emulsifying wax, 10% by w/w white soft paraffin, 10% w/w liquid paraffin, 5% by w/w propylene glycol, 0.1% by w/w chlorocresol, and water, wherein the composition is an emulsion.

17. The method according to claim 16, further comprising combining or admixing a second component in the form of at least one chemotherapeutic agent with a nuclear mechanism of action.

18. The method according to claim 16, further comprising removing free saccharides.

* * * * *